(12) United States Patent
Solis et al.

(10) Patent No.: US 12,191,027 B2
(45) Date of Patent: Jan. 7, 2025

(54) SNIP-TRIGGERED DIGITAL IMAGE REPORT GENERATION

(71) Applicant: HOLOGIC, INC., Marlborough, MA (US)

(72) Inventors: Herschel A. Solis, Santa Clara, CA (US); Edgar W. Chen, Newark, CA (US); Brian A. Garfinkel, Austin, TX (US)

(73) Assignee: Hologic, Inc., Marlborough, MA (US)

( * ) Notice: Subject to any disclaimer, the term of this patent is extended or adjusted under 35 U.S.C. 154(b) by 399 days.

(21) Appl. No.: 17/436,539

(22) PCT Filed: Mar. 27, 2020

(86) PCT No.: PCT/US2020/025443
§ 371 (c)(1),
(2) Date: Sep. 3, 2021

(87) PCT Pub. No.: WO2020/205610
PCT Pub. Date: Oct. 8, 2020

(65) Prior Publication Data
US 2022/0172824 A1 Jun. 2, 2022

Related U.S. Application Data

(60) Provisional application No. 62/826,011, filed on Mar. 29, 2019.

(51) Int. Cl.
*G16H 30/40* (2018.01)
*G16H 10/60* (2018.01)
(Continued)

(52) U.S. Cl.
CPC ............. *G16H 30/40* (2018.01); *G16H 10/60* (2018.01); *G16H 15/00* (2018.01); *G16H 30/20* (2018.01)

(58) Field of Classification Search
CPC ........ G16H 30/40; G16H 10/60; G16H 15/00; G16H 30/20
(Continued)

(56) References Cited

U.S. PATENT DOCUMENTS 3,502,878 A 3/1970 Stewart
3,863,073 A 1/1975 Wagner
(Continued)

FOREIGN PATENT DOCUMENTS

CN 108135580 6/2018
EP 775467 5/1997
(Continued)

OTHER PUBLICATIONS

International Search Report and Written Opinion of the International Searching Authority for International Patent Application No. PCT/US2020/025443 dated Jul. 3, 2020, 10 pages.
(Continued)

*Primary Examiner* — Michael R Neff
(74) *Attorney, Agent, or Firm* — Merchant & Gould P.C.

(57) ABSTRACT

Breast image analysis systems and computer-implemented method for snip-triggered digital image report generation. An image review workstation of breast image analysis system presents an interactive user interface including a currently displayed image to a user through a display. Image review station receives user input selecting a snipping application of interactive user interface and activating a snipping application. A portion of currently displayed image is selected by execution of snipping application, and in response, image review workstation accesses a data store of acquired image files, identifies an acquired image file associated with currently displayed image, and generates a digital image report comprising the selected portion of the currently displayed image and selected metadata of the
(Continued)

identified acquired image file and may also include user annotations such as spoken remarks and measurements and system generated data.

25 Claims, 10 Drawing Sheets

(51) Int. Cl.
  *G16H 15/00* (2018.01)
  *G16H 30/20* (2018.01)
(58) Field of Classification Search
  USPC .......................................................... 382/128
  See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels et al. |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch et al. |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,404,152 A | 4/1995 | Nagai |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,515,685 B1 | 2/2003 | Halverson |
| 6,525,713 B1 | 2/2003 | Soeta et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,751,780 B1 | 6/2004 | Neff et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,630,533 B2 | 12/2009 | Ruth et al. |
| 7,702,142 B2 | 4/2010 | Ren et al. |
| 7,760,924 B2 | 7/2010 | Ruth et al. |
| 7,840,905 B1 | 11/2010 | Weber |
| 8,239,784 B2 | 8/2012 | Hotelling |
| 8,571,289 B2 | 10/2013 | Ruth et al. |
| 8,712,127 B2 | 4/2014 | Ren et al. |
| 8,799,013 B2 | 8/2014 | Gustafson |
| 8,842,806 B2 | 9/2014 | Packard |
| 9,084,579 B2 | 7/2015 | Ren |
| 9,795,357 B2 | 10/2017 | Carelsen |
| 9,811,758 B2 | 11/2017 | Ren |
| 9,962,138 B2 | 5/2018 | Schweizer |
| 10,076,295 B2 | 9/2018 | Gemmel |
| 10,111,631 B2 | 10/2018 | Gkanatsios et al. |
| 10,206,644 B2 | 2/2019 | Kim |
| 10,248,882 B2 | 4/2019 | Ren |
| 10,679,095 B2 | 6/2020 | Ren |
| 10,922,897 B2 | 2/2021 | Maeda |
| 11,650,672 B2 | 5/2023 | Mellett |
| 11,857,358 B2 | 1/2024 | Liu |
| 2001/0038681 A1 | 11/2001 | Stanton et al. |
| 2001/0038861 A1 | 11/2001 | Hsu et al. |
| 2002/0012450 A1 | 1/2002 | Tsujii |

(56) References Cited

U.S. PATENT DOCUMENTS

| | | |
|---|---|---|
| 2002/0050986 A1 | 5/2002 | Inoue et al. |
| 2002/0075997 A1 | 6/2002 | Unger et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0149364 A1 | 8/2003 | Kapur |
| 2003/0194050 A1 | 10/2003 | Eberhard et al. |
| 2003/0194051 A1 | 10/2003 | Wang et al. |
| 2003/0194115 A1 | 10/2003 | Kaufhold et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0001094 A1 | 1/2004 | Unnewehr |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0140656 A1 | 6/2005 | McLoone |
| 2005/0226375 A1 | 10/2005 | Eberhard et al. |
| 2006/0026535 A1 | 2/2006 | Hotelling |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0021877 A1* | 1/2008 | Saito ................... G16H 30/20 |
| 2008/0045833 A1 | 2/2008 | Defreitas et al. |
| 2008/0109740 A1 | 5/2008 | Prinsen et al. |
| 2008/0130979 A1 | 6/2008 | Ren et al. |
| 2008/0187095 A1 | 8/2008 | Boone |
| 2008/0262874 A1 | 10/2008 | Toshimutsu |
| 2008/0267467 A1 | 10/2008 | Sokulin et al. |
| 2009/0003519 A1 | 1/2009 | Defreitas et al. |
| 2009/0010384 A1 | 1/2009 | Jing et al. |
| 2009/0033522 A1 | 2/2009 | Skillman |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0174663 A1 | 7/2009 | Rudd |
| 2009/0213034 A1 | 8/2009 | Wu et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0083154 A1 | 4/2010 | Takeshita |
| 2010/0086188 A1 | 4/2010 | Ruth et al. |
| 2010/0135558 A1 | 6/2010 | Ruth et al. |
| 2010/0194682 A1 | 8/2010 | Orr |
| 2010/0195882 A1 | 8/2010 | Ren et al. |
| 2010/0226475 A1 | 9/2010 | Smith et al. |
| 2010/0325088 A1 | 12/2010 | Hsieh et al. |
| 2011/0137132 A1 | 6/2011 | Gustafson |
| 2011/0270358 A1 | 11/2011 | Davis |
| 2011/0282686 A1* | 11/2011 | Venon ................... G16H 80/00 715/753 |
| 2011/0314405 A1 | 12/2011 | Turner |
| 2012/0131498 A1 | 5/2012 | Gross et al. |
| 2012/0133600 A1 | 5/2012 | Marshall et al. |
| 2012/0154431 A1 | 6/2012 | Fram |
| 2012/0275656 A1 | 11/2012 | Boese et al. |
| 2013/0239063 A1 | 9/2013 | Ubillos |
| 2013/0259193 A1 | 10/2013 | Packard |
| 2014/0013280 A1 | 1/2014 | Yoshioka et al. |
| 2014/0033126 A1 | 1/2014 | Kreeger |
| 2014/0123183 A1 | 5/2014 | Fujimoto |
| 2014/0140604 A1 | 5/2014 | Carton et al. |
| 2014/0143710 A1 | 5/2014 | Zhao |
| 2014/0282216 A1 | 9/2014 | Baker |
| 2014/0314205 A1 | 10/2014 | Carelsen |
| 2015/0094581 A1 | 4/2015 | Butler |
| 2015/0260816 A1 | 9/2015 | Liang |
| 2015/0309712 A1 | 10/2015 | Marshall et al. |
| 2015/0317434 A1 | 11/2015 | Kondo |
| 2015/0374325 A1 | 12/2015 | Shimizu |
| 2016/0162163 A1 | 6/2016 | Park et al. |
| 2016/0166222 A1 | 6/2016 | Kim |
| 2016/0235386 A1 | 8/2016 | Schweizer |
| 2016/0296185 A1 | 10/2016 | Gemmel |
| 2016/0364122 A1 | 12/2016 | Shimomura |
| 2016/0367120 A1 | 12/2016 | Dupont et al. |
| 2017/0038914 A1 | 2/2017 | Kawagishi |
| 2017/0065238 A1 | 3/2017 | Smith et al. |
| 2018/0137385 A1 | 5/2018 | Ren |
| 2018/0211421 A1 | 7/2018 | Wicklein |
| 2019/0196662 A1 | 6/2019 | Mitchell |
| 2019/0221046 A1 | 7/2019 | Maeda |
| 2019/0325255 A1 | 10/2019 | Ren |
| 2020/0363877 A1 | 11/2020 | Mellett |
| 2020/0373013 A1* | 11/2020 | Cao ................... G06T 7/0014 |
| 2022/0015731 A1 | 1/2022 | Liu |
| 2022/0020475 A1 | 1/2022 | Chen et al. |
| 2023/0107616 A1 | 4/2023 | Saba |

FOREIGN PATENT DOCUMENTS

| | | |
|---|---|---|
| EP | 982001 | 3/2000 |
| EP | 1004957 | 5/2000 |
| EP | 1428473 | 6/2004 |
| EP | 2783632 | 10/2014 |
| EP | 2913769 | 9/2015 |
| EP | 2952376 | 12/2015 |
| JP | 2000-322198 | 11/2000 |
| JP | 2004-038947 | 2/2004 |
| JP | 2004-357789 | 12/2004 |
| JP | 2007-029260 A | 2/2007 |
| JP | 2007-282656 | 11/2007 |
| JP | 2007-330374 | 12/2007 |
| JP | 2008-503253 | 2/2008 |
| JP | 2008-073436 | 4/2008 |
| JP | 2008-199293 | 8/2008 |
| JP | 2010-086149 | 4/2010 |
| JP | 2014-068874 | 4/2014 |
| JP | 2014-104099 | 6/2014 |
| JP | 2017-000664 | 1/2017 |
| WO | 1990/05485 | 5/1990 |
| WO | 1998/16903 | 4/1998 |
| WO | 00/51484 | 9/2000 |
| WO | 03/020114 | 3/2003 |
| WO | 2005/051197 | 6/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2011/044295 | 4/2011 |
| WO | 2011/066486 A2 | 6/2011 |
| WO | 2012/071429 A1 | 5/2012 |
| WO | 2014/183183 | 11/2014 |
| WO | 2018/183548 | 10/2018 |
| WO | 2018/183549 | 10/2018 |

(56) References Cited

FOREIGN PATENT DOCUMENTS

| WO | 2018/183550 | 10/2018 |
|---|---|---|
| WO | 2019/032558 | 2/2019 |

OTHER PUBLICATIONS

PCT International Preliminary Report on Patentability in Application PCT/US2020/025443, mailed Oct. 14, 2021, 9 pages.
"Layer Basics—Adobe Press", published Apr. 6, 2017; https://www.adobepress.com/articles/article.asp?p=2756476&seqNum=4.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98/5493, Nov. 1998.
Dobbins JT et al. "Digital x-ray tomosynthesis: current state of the art and clinical potential" Physics in Medicine and Biology vol. 48, No. 19, pp. 65-81 (2003).
Essentials for life: Senographe Essential Full-Field Digital Mammography System, GE Health-care Brochure, MM-0132-05.06-ENUS, 2006.
Filtered Back Projection, (NYGREN) published May 8, 2007; URL: http://web.archive.org/web/1999101013 | 715/http://www.owlnet.rice.edu/-elec539/Projects97/cult/node2.html.
Grant, DG, "Tomosynthesis, a three dimensional imagine technique", IEEE Trans. Biomed Engineering, vol. BME-19, #1, Jan. 1972, pp. 20-28.
Heang-Ping Chan et al., "ROC study of the effect of stereoscopic imaging on assessment of breast lesions", Medical Physics, vol. 32, No. 4, Apr. 2005.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Lorad Selenia Document B-BI-SEO US/Intl (May 2006) copyright Hologic 2006.
Mammographic Accreditation Phantom, http://www.cirsinc.com/pdfs/015cp.pdf.
Pediconi, Federica et al., "Color-coded automated signal intensity curve for detection and characterization of breast lesions: Preliminary evaluation of a new software for MR-based breast imaging", International Congress Series 1281 (2005) 1081-1086.
Senographe 700 & 800T (GE); 2-page download on Jun. 22, 2006 from www.gehealthcare.com/inen/rad/whe/products/mswh800t.html.; Figures 1-7 on 4 sheets relateral shift compression paddle.
Smith, A., "Fundamentals of Breast Tomosynthesis", White Paper, Hologic Inc., WP-00007, Jun. 2008.

\* cited by examiner

| Simple editor | Detailed editor | | |
|---|---|---|---|
| List only tags COMMON to ALL files ▼ | 315 tags displayed (total = 315 tags) | | |
| | [Group, Element] | Title | Value |
| All existing tags | | | |
| Variant tags | | | |
| Critical tags | | | |
| [0002] File Meta Elements | | | |
| [0008] Study information | 0010-0000 | Patient Group Length | 92 |
| [0009] Private | 0010-0010 | Patient's Name | XXXXXXXX |
| [0010] Patient | 0010-0020 | Patient ID | EX/10/00832 |
| [0011] Private | 0010-0030 | Patient's Birth Date | 19640101 |
| [0018] Acquisition Group | 0010-0040 | Patient's Sex | |
| [0019] Private | 0010-1010 | Patient's Age | 000Y |
| [0020] Acquisition Group | 0010-1030 | Patient's Weight | 80 |
| [0021] Private | 0010-2180 | Additional Patient History | |
| [0023] Private | 0011-0000 | Group Length | 30 |
| [0025] Private | 0011-0010 | Inconnu | GEMS_PATI_01 |
| [0027] Private | 0011-1010 | Inconnu | Num=0 Str= |
| [0028] Image presentation | 0018-0000 | Aquisition Group Length | 482 |
| [0029] Private | 0018-0020 | Scanning Sequence | SE |
| [0040] Private | 0018-0021 | Sequence Variant | NONE |
| [0043] Pixel Data | 0018-0022 | Scan Options | SAT_GEMS\VB_GEMS\FILTERED_GEMS\SP |
| [7FE0] | 0018-0023 | MR Acquisition Type | 2D |
| Tags to modify | 0018-0025 | Angio Flag | N |
| Tags to add | 0018-0050 | Slice Thickness | 5 |
| Tags to remove | 0018-0080 | Repetition Time | 3000 |
| Search | 0018-0081 | Echo Time | 92.976 |
| | 0018-0082 | Inversion Time | 0 |
| | 0018-0083 | Number of Averages | 2 |
| | 0018-0084 | Imaging Frequency | 63.867787 |

FIG. 7B

SNIP-TRIGGERED DIGITAL IMAGE REPORT GENERATION

This application is a National Stage Application of PCT/US2020/025443, filed on Mar. 27, 2020, which claims priority to and the benefit of U.S. Provisional Application No. 62/826,011, filed on Mar. 29, 2019. Those applications are incorporated herein by reference in their entireties. To the extent appropriate, a claim of priority is made to each of the above disclosed applications.

FIELD OF INVENTION

Embodiments of the invention relate to medical imaging, and more particularly, to breast image acquisition and review systems and interactive user interfaces thereof.

BACKGROUND

Many people have suffered from breast cancer and other types of cancers, and early detection is key to increasing chances of survival. One manner of analyzing breast tissue for cancer is imaging a patient's breast, which may be performed using various imaging modalities such as X-ray mammography imaging, tomosynthesis imaging, magnetic resonance imaging (MRI) and ultrasound imaging. One example of an image acquisition device is Selenia® Dimensions® digital mammography system with acquisition workstation available from Hologic, Inc., Marlborough, MA Selenia® and Dimensions® are registered trademarks of Hologic, Inc. Acquired images are reviewed by a radiologist to identify abnormalities or irregularities such as microcalcifications, lesions and tumors.

The radiologist may review breast tissue images using an interactive diagnostic tool in the form of an image review workstation. Examples of image review workstations include the image review workstation of the Selenia® Dimensions® digital mammography system noted above and SecurView® image review workstation also available from Hologic, Inc. SecurView® is also a registered trademark of Hologic, Inc. An image review workstation provides for diagnostic viewing of generated images while providing for an image review workflow of various images and for images acquired with various imaging modalities.

Current image review workstations have been effectively utilized for diagnostic review, but image review workstations can be improved from the perspective of both engineers who design the workstation's hardware and software components and radiologists who use the image review workstation for diagnostic review of breast images.

For example, an engineer may be required to review images to identify and resolve hardware and software bugs, one example of which involves inconsistent images when using different system configurations or software programs despite images being based on the same acquisition data. A particular part of an image may appear enhanced or washed out when the image review workstation executes one software program compared to that same part of the image when the image review workstation executes another software program or software version. Image inconsistencies may result in inaccurate diagnosis, such as false positives or false negatives, if not resolved. The engineer may troubleshoot the cause of hardware and software bugs by reviewing various images and focusing on particular inconsistent portions thereof in order to identify and attempt to resolve image inconsistencies. Troubleshooting effectiveness may be impacted due to the image processing software bugs being difficult to replicate and difficult to track since engineers often review various aspects of a particular image, investigate multiple images, and may also review different sets or series of images for a particular patient. Navigating and reviewing images while attempting to focus on particular parts thereof and recording troubleshooting details can be difficult and time consuming, and the resulting recorded details may not be comprehensive.

As another example, a radiologist reviews a series of images during a review workflow and focuses in and out on particular portions thereof in order to assess potential tissue abnormalities. Radiologists may be interrupted during workflows to manually record notes and observations about images being reviewed. These interruptions are disruptive to the workflow process, and radiologists may only record a portion of information that is pertinent or that should be noted for subsequent review. For example, a radiologist's workflow may be performed in a dark environment to review multiple images during a review session and workflow disruptions may affect one or more or all of radiologist productivity, efficiency and quality or accuracy of image assessment. These inconveniences and shortcomings are compounded as more images are reviewed as part of the radiologist's workflow.

Engineers and radiologists also face problems when using current image review workstations since they are not able to effectively capture metadata (patient, study, series, image), user generated input (e.g. annotations, measurements), and system generated input (e.g. kinetics and Computer Aided Detection (CAD) data) in an efficient manner during image review. Radiologists, for example, are not able to effectively capture information quickly and precisely in order to minimize user error (e.g., reporting on a wrong breast, view or study) and improve efficiency when reporting on findings during patient review while also being able to, for example, export information and findings into other formats and for integration into a third party reporting system or a presentation.

Thus, there exists a need for more improved image review workstations. There also exists a need for more effective, efficient and comprehensive generation of reports for image review workstation troubleshooting and image review workflows and that do not disrupt a user's workflow during image review while reducing user error and providing for efficient and effective reporting and reporting exportation.

SUMMARY

Embodiments of the invention relate to computerized image analysis systems and execution of automated actions by a computerized image analysis system in response to pre-determined user interactions with a user interface during display of an acquired image.

Embodiments of the invention are also related to computerized image and analysis systems that automatically generate or at least partially populate a digital report concerning one or more images. Embodiments may execute automatically, without manual entry of user data, image metadata or system generated data. Embodiments may also incorporate certain user provided data in the form of user annotations provided during image review (e.g., verbal notes and measurements drawn by a user) and before a digital image report is generated and system generated data or data generated by at least one of an image review workstation and an image acquisition device (e.g., CAD and kinetics information such as worst curve post-processed by the image review workstation). Embodiments may also completely or at least partially populate a digital image report and may do so using a template having a pre-defined structure to be populated.

Certain embodiments involve automated image report generation by an image review workstation in response to activation or execution of a snipping application and selection of a portion of a currently displayed image.

Certain embodiments provide for integrated, real-time, in-flow data capture. Data captured during a review workflow may include one or more or all of, and different combinations of, currently displayed image or portion thereof, non-displayed related image or portion thereof, user annotations, image metadata and system generated data. The generated image report can eliminate or substantially reduce manual data entry during image review while not disrupting review workflows.

Certain embodiments relate to snip-triggered image report generation. Embodiments allow an image review workstation to automatically generate a digital image report that may include one or more or all of user annotation, a currently displayed image that is the subject of user navigation or selected portion thereof, a non-displayed image or portion thereof, displayed or non-displayed image metadata and system generated data. In this manner, a user can snip or select a portion of a displayed image and that snipped or selected portion and other associated data is automatically captured and integrated into an image report. For example, the generated image report may include certain metadata read from an acquired image file such as one or more of patient demographic data, study and series data, image acquisition data such as image acquisition device, configuration, modality and parameter data and system generated data resulting from post processing performed by an image review workstation. Thus, with embodiments, a digital image report may be automatically generated to include the snipped or selected portion of an image that was of interest together with one or more of preferred or pertinent image file metadata, system generated data and user annotation data without requiring the user to remember or manually enter such data after a snipping action has been initiated.

According to one embodiment, image report generation is triggered in response to a portion of an image presented through an interactive UI of the image review station being selected or snipped.

One embodiment involves a computer-implemented method executed by an image review workstation of a breast image analysis system and includes the image review workstation presenting, through a display, an interactive user interface including a currently displayed image of a subject's breast tissue. The image review station automatically generates a digital image report that includes a portion of the currently displayed image in response to selection of a portion of the currently displayed image by execution of a snipping application of the interactive user interface.

Another embodiment involves a computer-implemented method executed by an image review workstation of a breast image analysis system and includes the image review workstation presenting, through a display and to a user of the image review workstation, in response to selection of a portion of the currently displayed image, and automatically generating a digital image report including the selected portion of the currently displayed image and certain other data such as metadata or a subset of metadata of an image file associated with the currently displayed image.

A further embodiment involves a computer-implemented method executed by an image review workstation of a breast image acquisition and review system to automatically generate a digital image report. The digital image report is generated in response to a user snipping a portion of a currently displayed image presented in an interactive user interface generated by the image review workstation, and the generated digital image report is transmitted by the image review workstation through a communication network to a computing device. The digital image report can be subsequently presented to a user of the computing device.

In one embodiment, a computer-implemented method executed by an image review workstation of a breast image analysis system includes the image review workstation presenting, through a display and to a user of the image review workstation, an interactive user interface comprising a currently displayed image of a breast tissue of a subject. The image review station receives user input selecting or launching a snipping application of the interactive user interface. The snipping application is activated and executed by a processor of the image review workstation executing computer-executable instructions of the snipping application stored in a non-transitory computer-readable medium. A portion of the currently displayed image is selected by execution of the snipping application. The computer-implemented further comprises the image review workstation, in response to selection of the portion of the currently displayed image, accessing a data store including acquired image files that include respective image data and respective metadata associated with respective breast tissue images, identifying an acquired image file associated with the currently displayed image, and generating a digital image report. The digital image report may include one or more or all of the currently displayed image and selected portion thereof, a related image that is not currently displayed and a selected portion thereof, image metadata, pre-snip user annotations and system generated data such as CAD and kinetics data. For example, the digital image report may include the selected portion of the currently displayed image and selected metadata of the identified acquired image file.

In another embodiment, a computer-implemented method comprises presenting, through a display of an image review workstation of a breast image analysis system and to a user of the image review workstation, an interactive user interface comprising a currently displayed image of a breast tissue of a subject. The image review station receives user input selecting a snipping application of the interactive user interface and activates the snipping application by executing computer-executable instructions stored in a non-transitory computer-readable medium, wherein a portion of the currently displayed image is selected by execution of the snipping application. The image review workstation, in response to selection of the portion of the currently displayed image, accesses a data store including acquired image files. The image review station generates a digital image report comprising the selected portion of the currently displayed image and selected metadata of the identified acquired image file and system generated data such as data generated by a CAD or post MRI processor. Thus, embodiments provide for snip-triggered generation of a digital image report including a currently displayed image or portion thereof and system generated data, and may, in certain embodiments, include one or more or all of user annotations, image file meta data, additional image data and system generated data.

In one or more embodiments, the generated digital image report may also include one or more or all of image data such as pixel data of the currently displayed image or selected portion thereof, the currently displayed image such that the image report includes the entire currently displayed image and the particular section of interest that was selected or snipped during review.

In one or more embodiments, metadata read from an acquired image file and included in an image report may include one or more or all of patient demographic data, study and series data, and image acquisition data such as imaging modality or type of image device utilized and operating parameters thereof. Image file metadata to be included in the digital image report is selected by the user of the image review workstation before activation of the snipping application, and before snipping or selection of a portion of a currently displayed image. Pre-snipping metadata selection may involve a user interface with types of metadata included in the image file so that the user can select metadata of interest for the image report to be generated. In other embodiments, metadata included in the digital image report is selected by the user of the image review workstation in real-time or in-flow during review of the currently displayed and after execution of the snipping application, e.g., after a portion of a currently displayed image has been selected or snipped.

In one or more embodiments, the snipping application is operable to select or snip a static image of the selected portion of the currently displayed image that is then included in the image report. The snipping application may also record a video or series of image frames of the user's interaction with the currently displayed image or interactive user interface such that the video included in the image report can be replayed. Embodiments may also involve generation of a digital image report that includes non-displayed images (e.g. images that are part of the same sequence such as a dynamic contrast-enhanced series or reconstructed images that may be captured at the same location but presented in different orthogonal planes or rendered in a different view for example in maximum intensity projection (MIP) versus slice data.

In one or more embodiments, the image review workstation is triggered to identify one or more views of the portion of the currently displayed image that was selected or snipped, and these other views may be included in the image report. The currently displayed image from which a portion is snipped or selected may be presented in a first view, and the image review workstation then accesses a data store of acquired image files to identify that selected portion of the currently displayed image in a second view different from the first view. The first and second (third, and additional as needed) views of the selected portion are included in the image report.

For example, the first view may be an axial view of the selected portion of the currently displayed image, whereas the second view is a sagittal view or a coronal view of the selected portion of the currently displayed image. In embodiments involving a third view, the first view can be an axial view of the selected portion of the currently displayed image, the second view can be a sagittal view of the selected portion of the currently displayed image, and the third view can be a coronal view of the selected portion of the currently displayed image. In another embodiment, the second view is in the form of a computer-generated rendering of the selected portion of the currently displayed image such as a MIP rendering, multiplanar reconstruction, a subtraction rendering, a CAD rendering or a MRI post-processed analysis such as dynamic contrast enhanced (DCE) colorization. Further, the first view may be a view of an acquired optical image of the subject's breast tissue, and the second view is a computer-generated rendering of the subject's breast tissue.

In one or more embodiments, the image review workstation is triggered to identify one or more additional currently displayed or non-displayed images in response to snipping or selection of a portion of the currently displayed image, and these one or more additional images are included in the image report. The entire additional image or a portion thereof corresponding to the selected portion of the currently displayed image may be included in the image report. The one or more additional images may be from the same acquired image file as the currently displayed image, e.g., both the currently displayed and additional image were acquired using the same image acquisition device and imaging modality. In other embodiments, the additional image was acquired using a different imaging modality and different image acquisition device, e.g., one image may have been acquired with a magnetic resonance imaging device, whereas other additional identified images were acquired with a tomosynthesis imaging device, an x-ray imaging device, or an ultrasound imaging device. Thus, different types of images and images generated using different acquisition systems and modalities may be included in an image report that is generated.

In one or more embodiments, user annotations are included in a generated image report and annotation monitoring may be activated to capture video, voice or interaction annotations during review of the currently displayed image. For these purposes, the image review workstation includes an input or peripheral device such as a keyboard, keypad, touchscreen, mouse, or microphone to receive real-time user annotations concerning the selected portion of the currently displayed image. User annotations may be in the form of typed annotations, e.g., via a keyboard, keypad, or touchscreen, identification annotations, e.g., using a mouse to point to a particular section of the currently displayed image, or voice annotations that provide a verbal summary, description or notes of the user's assessment. In certain embodiments, pre-snip annotations (e.g., measurement notes drawn on UI) are captured, and post-snip annotations (e.g., verbal remarks) may also be captured.

In one or more embodiments, the interactive user interface including the currently displayed image includes capture indicators for measurement (such as rule measurement), location and distance data associated with the selected portion of the current displayed image such as a lesion within the selected portion.

In one or more embodiments, the snipping application is activated in response to pre-determined user input such as selection of a pre-determined key of a computer keyboard, keypad or mouse of the image review workstation, pre-determined element of the interactive user interface, speaking a pre-determined voice prompt into a microphone of the image review workstation or a pre-determined gesture detected by a camera of the image review workstation during presentation of the currently displayed image.

In one or more embodiments, the image report that is generated by the image review workstation includes only the selected image portion or a plurality of image portions including the selected portion and a portion of at least one other image stored in the data store and corresponding to the selected portion of the currently displayed image. The other image portion can be incorporated into the image report without being presented to the user during image workstation review so that the user's workflow is not interrupted or complicated by presentation of other images which may be reviewed later in the image report.

In a one or more embodiments, snip-triggered image report generation may be executed by initially loading or creating a template in response to activation or execution of the snipping application. The template may be structured to include certain sections to be populated with the selected portion of the currently displayed image, certain sections for additional images or views, and certain other sections for other captured data. Thus, data of certain formats are integrated into respective template portions for respective formats (e.g., into corresponding image sections and into corresponding user annotation/verbal remark and video sections). The template is automatically populated by the image review workstation with captured images and data to generate the digital image report in response to user selection of the portion of the currently displayed image.

In a one or more embodiments, the image review workstation generates an image report in the same format utilized for storing acquired image files, e.g., a Digital Imaging and Communication in Medical (DICOM) format. In other embodiments, the image review workstation converts the currently displayed image or selected portion thereof from a first image format to a second image format for the digital image report, e.g., from a DICOM format into a JavaScript Object Notation (JSON) file, a Portable Document Format (.pdf) file, or a Portable Network Graphics (.png) image file. Images or selected image portions may be or converted into or be in a format such as Tagged Image File Format (.tiff), Joint Photographic Experts Group (.jpg) or Graphics Interchange Format (.gif). Conversion from one format to another may involve image conversions between image formats or a conversion involving a non-image format such as an audio file, a video file, a JSON file, a DICOM file, or a Health Level 7 (HL7) format. Thus, the report that is generated may result from different types of conversions and types of data and one or multiple conversions for respective types or sections of reports generated.

In one or more embodiments, after snip-triggered digital image report image generation, the image review workstation may present the generated digital image report to the user through the display of the image review workstation or execute other actions, e.g., after the review session has been completed, or execute other actions such as storing the digital image report to the data store so that the image report is associated with the acquired image file in the data store or transmitting the generated digital image report in an electronic mail message or using other types of communication or messaging protocols such as DICOM, Health Level 7 (HL7) and web to a separate computing device (generally, electronic message).

In one or more embodiments, the currently displayed image is encoded or associated with an identifier to the associated acquired image file stored in the data store and pointers to a subset of metadata in the identified image file that are to be included in the digital image report. For example, with DICOM image files, the currently displayed image is encoded with pointers to tagged portions of a DICOM file header, and the tagged data is included in the generated image report. In this manner, only a subset of available metadata or tagged data of an image file that is of interest to the radiologist such as certain demographic data, study and series data, and image acquisition data such as image acquisition device, configuration, modality and parameter data is incorporated into image report rather than all of the metadata of an image file or all of the tagged data of a DICOM file.

In one or more embodiments, the snipping application is executed by the image review workstation in response to user interaction with the image review workstation, but in other embodiments, the snipping application is executed by an image acquisition device in communication with the image review workstation and executed in response to user interaction with the image review workstation.

In one or more embodiments, the digital image report that is generated, whether partially or completed populated, may include one or more of a currently displayed image, a selected portion of the currently displayed image, one or more images that are not displayed or not currently displayed to the user, and a selected portion of an image that is not currently displayed. Images that are not currently displayed may be a related image for the patient from a prior study or a dynamic contrast-enhanced MRI series with multiple time points as examples, Thus, the generated digital image report may include a currently displayed image or portion thereof (e.g. pre-contrast series) and one or more non-displayed images (post contrast series).

Other embodiments include, without limitation, breast image analysis systems that include an image review workstation configured to execute computer-implemented methods, or that include both an image review workstation and image acquisition device.

Further embodiments include, without limitation, a non-transitory computer readable medium tangibly embodying one or more sequences of instructions wherein execution of the one or more sequences of instructions by one or more processors contained in a computing system of a breast image analysis system causes the computing system to automatically generate a digital image report.

While embodiments may be utilized by end users of an image review workstation such as a surgeon, radiologist or clinician, embodiments may also be utilized by a manufacturer of the image review workstation such as an engineer analyzing whether the image review workstation is working properly.

Thus, the embodiments disclosed and described herein address shortcomings of current image review workstations and interactive user interfaces thereof as well as user workflows during image reviews by reducing user error and streamlining a tedious, time consuming, inefficient and disruptive workflow process integral to computer-generated user interfaces of image review workstations and user interactions.

DETAILED DESCRIPTION OF ILLUSTRATED EMBODIMENTS

Figure 1:
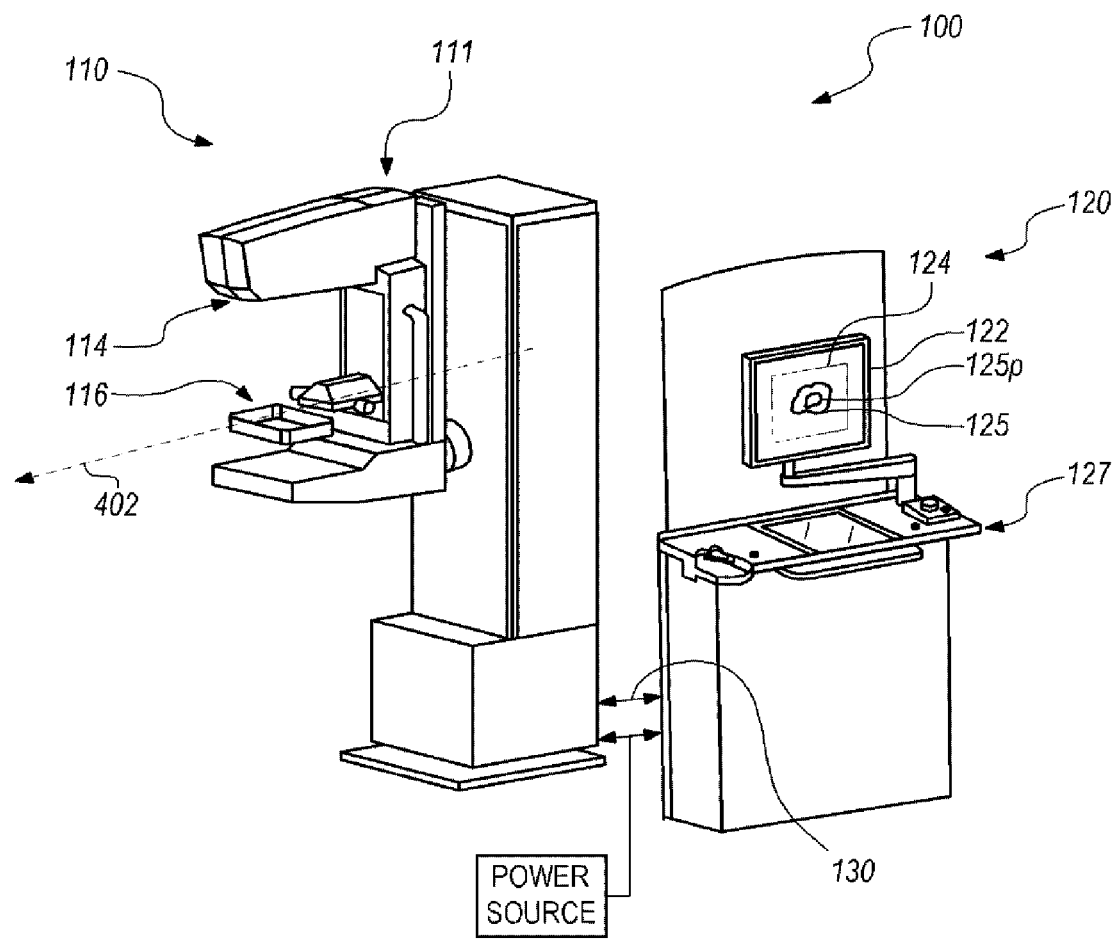
FIG. 1 is a perspective view of a breast image analysis system including an image acquisition device and image review workstation that can be configured to incorporate snipping application embodiments for snip-triggered digital image report generation.

Systems, methods, computer program products and interactive computer-generated user interfaces for snip-triggered generation of digital image reports during review or navigation of images presented through a display of an image review workstation. Embodiments provide for automated generation of an image report or portion thereof in response to a pre-determined user input during image review and during review of an image of interest while eliminating or reducing user input required to create a report while eliminating or reducing image review workflow interruptions. Embodiments execute in-line and in real time during image review to improve diagnostic image review workflows conducted by radiologists and troubleshooting image review workflows conducted by engineers.

Embodiments provide for automated digital image report generation during an image review workflow thus resulting in more efficient, convenient and comprehensive image review and report generation that also assists with reducing user errors while eliminating or reducing user input. Improvements provided by embodiments are further enhanced by snip-triggered capture of various types of pertinent data and generation of an image report including same such as selected metadata of an image file such as a Digital Imaging and Communications in Medicine (DICOM) file. In this manner, only certain metadata of interest to the user, e.g., a subset of the hundreds of different types of metadata in a DICOM file header, are automatically incorporated into a digital image report together with the selected portion of the currently displayed image and other associated images if so configured. Embodiments provide for image review workstations that are more efficient and user friendly and that generate more comprehensive digital image reports to facilitate image reviews and reduce user errors without disrupting the review workflow as a result of executing while the user is already interacting with the currently displayed image of interest. In this manner, the user is not required to stop and start review to execute another program or record notes regarding the currently displayed (or other) image.

Embodiments provide for transmission of the digital image report to another computer device. The other computer device can be either an image review workstation or any other device that allows viewing of the report generated by using the snip-triggered capture. In this way, a radiologist creating a radiology report can pass on the information gleamed from the review to another reviewer. Radiologists commonly spend a significant amount of time reviewing multiple images including different image views, imaging modalities and image manipulations as part of the diagnosis of cancer. Another reviewer subsequently picking up a patient case, for example for purposes of second review, biopsy, or additional imaging, would have to duplicate the same reviewing of different image views, imaging modalities and image manipulations in order to find the same region of interest identified by the first reviewer. Such work is duplicative and inefficient. By using the snip-triggered capture, any subsequent reviewer would have the information for the reasons for the first radiologist's diagnosis as well as the snip-triggered image of the region of interest in one report.

In addition, the comprehensive digital image reports can be used as part of patient reporting obligations. After the radiologist reaches the diagnosis, the diagnosis is communicated to the patient. The report communicated would be improved by including a specific image of interest as part of the report. The patient would be benefited from the information and could also use that information for subsequent diagnosis and treatment, partially by another location.

Exemplary medical imaging environments in the form of breast image analysis systems in which embodiments may be implemented are described with reference to FIGS. 1-2, and embodiment configurations and operation relative to these exemplary systems and environments are described with reference to FIGS. 3-10.

FIG. 1 depicts one example of a medical imaging environment or breast image analysis system 100 (generally, breast image analysis system) that may be adapted, configured or programmed to execute embodiments of snip-triggered digital image report generation. FIG. 1 depicts breast image analysis system 100 including an image acquisition device 110 and an acquisition workstation 120 in communication with each other through a communication link or network 130. Image acquisition device 110 may utilize various imaging modalities. One example of image acquisition device 110 is a tomosynthesis acquisition system.

One exemplary image acquisition device 110 as depicted in FIG. 1 includes a rotatable tube arm assembly 112 carrying an x-ray tube assembly 114. Other imaging devices may be utilized, but for ease of explanation, FIG. 1 is described with reference to image acquisition device 110 including an X-ray imaging device. X-ray tube assembly 112 includes an x-ray tube generating x-ray energy to image a patient's breast tissue compressed between a support base and compression plate assembly 116. Image acquisition device 110 can operate in different modes including standard mammography mode and tomosynthesis mode. Acquired images are stored in a data store or archive, e.g., a Picture Archive and Communication System (PACS) archive, and image files for acquired images are generated by image acquisition device 110 according to an imaging standard, one example of which is Digital Imaging and Communications in Medicine (DICOM). The DICOM standard provides a consistent platform for handling, storing, printing, and transmitting information in medical imaging and uses a specified file format and communications protocol.

FIG. 1 depicts an acquisition workstation 120 including one or more displays 122 (typically flat panel display that may include touchscreen functionality) through which an interactive UI 124 including one or more currently displayed images 125 is presented to a user or viewer (generally, user, such as technologist). Image acquisition workstation 120 also includes one or more input or peripheral devices 127 such as a keyboard, keypad, mouse, trackball, touchscreen, microphone for detection of voice commands, and a camera for video acquisition and user gesture or motion detection.

Figure 2:
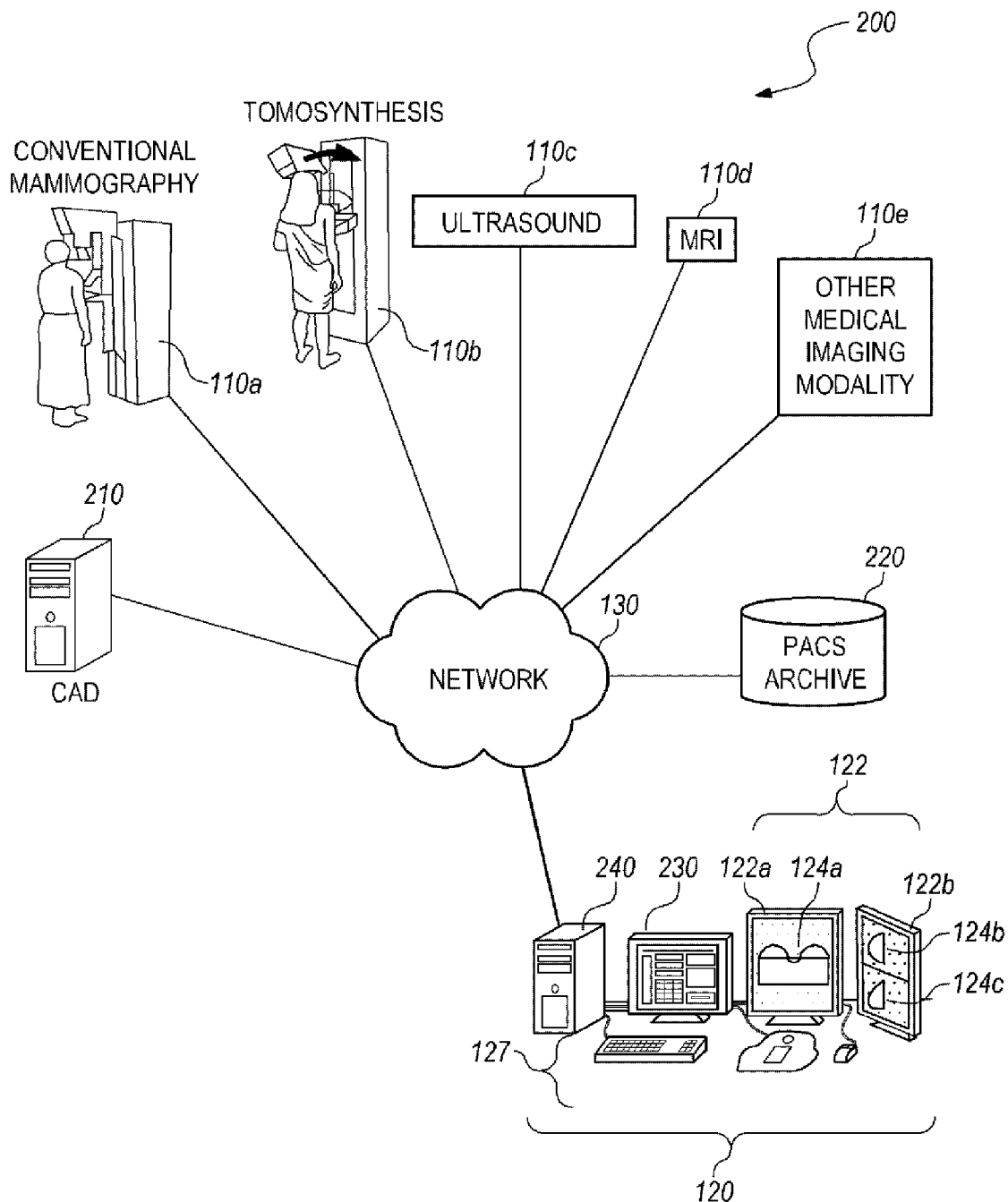
FIG. 2 is a perspective view of another breast image analysis system including an image acquisition device and image review workstation that can be configured to incorporate snipping application embodiments for snip-triggered digital image report generation.

FIG. 2 depicts a breast image analysis system 200 including one or multiple image acquisition devices 110 and image review workstation 120A in communication with each other through network 130. FIG. 2 illustrates breast image analysis system 200 that may include one or multiple image acquisition devices 110 such as a conventional mammography acquisition device 110a, a tomosynthesis acquisition device 110b, an ultrasound acquisition device 110c, a magnetic resonance imaging (MRI) acquisition device 110d, and a generalized "other" medical imaging device 110e representative of, for example, one or more computerized tomography (CT) imaging or positron emission tomography (PET) acquisition devices. Image review workstation 120A may include one or more displays 122a-b (generally display) with respective interactive UIs 124a-c or output windows (generally, interactive UI) with which user can interact and that can be navigated using one or more user input or peripheral devices 127. Image review workstation 120A as depicted in FIG. 2 also includes an administrative display 230 for used for input and output of information associated with a particular set of images such as listings, tables, plots, text descriptions, etc. and system information. Image review workstation 120A interactively displays the medial images to user in accordance with one or more UI programs carried out on an UI controller or processor 240.

Breast image analysis system 200 may also include one or more image processing systems or programs in communication with network 130. One example of processing system or program 210 for system generated data is a computer-aided detection (CAD) processor. A CAD processor that receives digital medical images from one or more image acquisition devices 110 to execute one or more CAD algorithms and generates system data in the form of CAD findings is provided. Another example of processing system or program 210 for system generated data is a post-Magnetic Resonance Imaging (MRI) processor for executing breast Dynamic Contrast Enhanced (DCE) colorization and providing kinetic findings (e.g., worst curve, post-processed by the system). While embodiments may involve different types of system generated data and associated processors or systems, reference is made generally to a system generated data generated by a CAD processor 210 as a non-limiting example.

Digital images acquired with one or more image acquisition devices 110 are stored to a data store or archive 220 (generally, data store), one example of which is a Picture Archiving and Communication System (PACS) archive. Data store 220 generally represents a repository for medical information associated with breast image analysis system 200, including both current and archived images, current and archived system generated data such as CAD results, radiology reports for completed cases, and so forth.

Interactive UI 124 implemented at image review workstation 120A interactively displays medical images 125 to a viewer or user via display 122. Various medical images and related information are communicated according to the DICOM standard and network 130 supports the TCP/IP protocol, which is used as the transport protocol for the DICOM standard.

Further aspects of exemplary image acquisition devices 110, image review workstations 120A, data stores 130 such as PACS archives, and networked medical imaging environments are described in U.S. Publication No. 2017/0065238A1, published on Mar. 9, 2017, U.S. application Ser. No. 15/537,326, entitled "METHODS AND SYSTEMS FOR DYNAMICALLY MODIFYING ACQUISITION PARAMETER DURING IMAGE ACQUISITION," which is commonly owned by Hologic, Inc., Marlborough, MA, and International Publication Number WO 2012/071429 A1, PCT Application No. US2011/061875, entitled "USER INTERFACE FOR MEDICAL IMAGING REVIEW WORKSTATION," which is also owned by and names Hologic, Inc. as Applicant, the contents of which are also incorporated herein by reference as though set forth in full.

Breast image analysis systems constructed and operable according to embodiments and described in further detail with reference to FIGS. 3-10 include a snipping application incorporated into image review workflow presented by image review workstation 120A during review of currently displayed image 125 and is seamlessly integrated into an existing medical imaging workflow. According to embodiments, image review workstation 120A is triggered to automatically generate a digital image report or certain portion thereof based on pre-determined user interaction with interactive UI 124. According to one embodiment, image review workstation 120A is triggered to automatically generate a digital image report or a portion thereof in response to execution of snipping application to select a portion of currently displayed image 125 presented through interactive UI 124, thus providing for automated, efficient and comprehensive digital image reports and complete or partial digital report generation while eliminating or reducing workflow interruptions during image review and troubleshooting.

Figure 3:
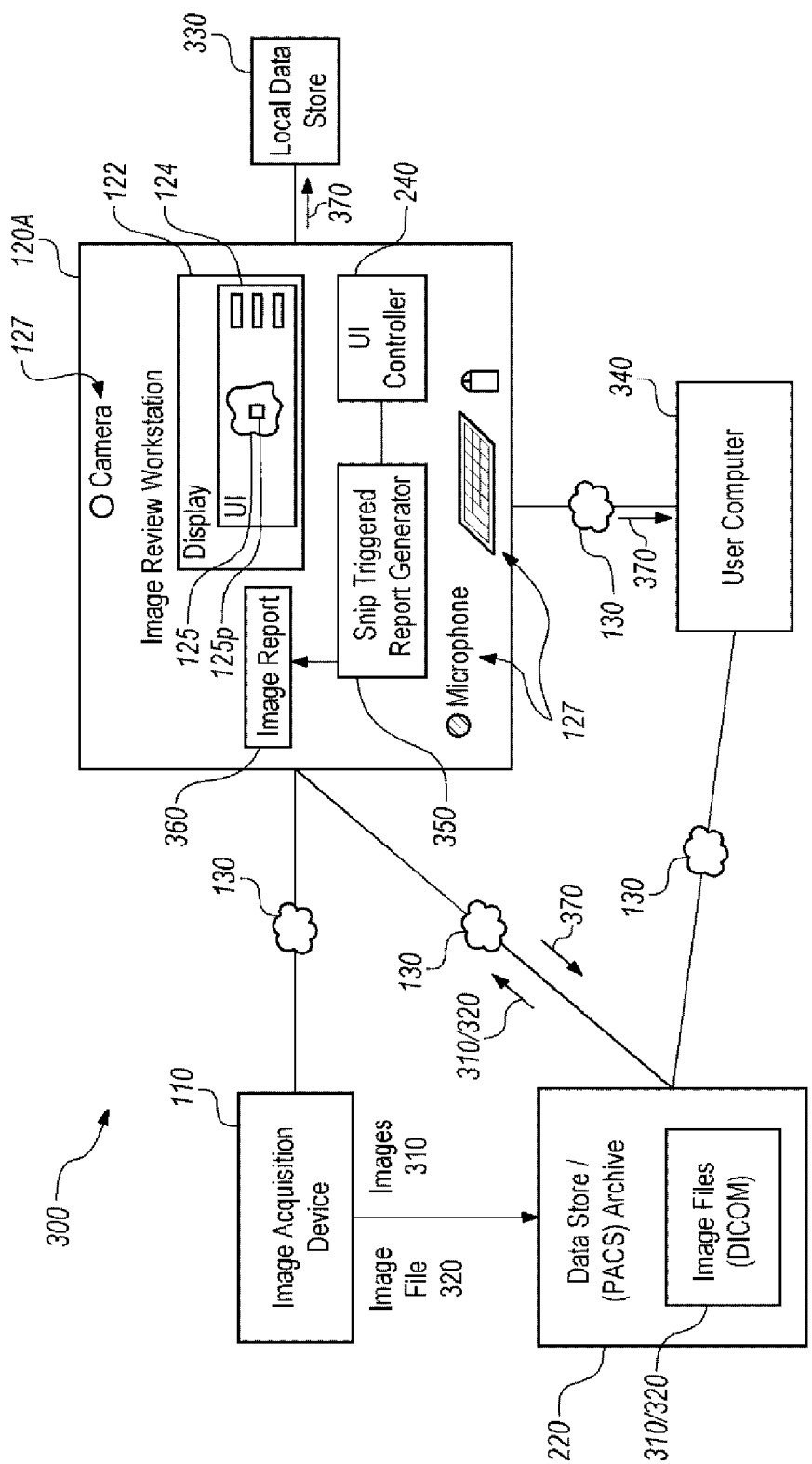
FIG. 3 is a system block diagram of a breast image analysis system constructed according to one embodiment and including a snipping application executed by an image review workstation according to one embodiment.

FIG. 3 depicts an embodiment of a breast image analysis system 300 including image acquisition device 110 that generates breast tissue images 310 and corresponding images files 320 for acquired breast tissue images 310. Image files 320 including image or image data 310 are stored in data store 220 such as PACS archive in communication with image acquisition device 110 and according to the DICOM standard (DICOM file or image file 320 in FIG. 3). Data store 220 typically stores image files 320 for a multitude of patients. Image review workstation 120A is in communication with data store 220 to read or access image files 320 and display images 310 through interactive UI 124 as described above with reference to FIGS. 1-2. Image review workstation 120A may also be in communication with a different or local data store 330 for storing copied or local image files 310 and/or images 320. Image review station 120A may also be in communication with a separate computing device 340 such as a computer of a user of another image review workstation 120A.

According to embodiments, image review workstation 120A includes computer-executable instructions of a snip-triggered digital image report generation application 350 (referred to as snipping application) stored in a non-transitory computer readable medium executable by a processor of image review workstation 120A. Snipping application 350 is in communication with, utilized by or an executable component of UI controller 240, which generates and modifies interactive UI 124 through display 122 of image review workstation 120A such that UI controller 240 output results in presentation of currently displayed image 125 to user, and when snipping application 350 is executed, currently displayed image 125 is maintained or set as a background or working image by UI controller 240. User is thus able to manipulate input or peripheral device 127 such as a touchscreen, keypad, keyboard, mouse or other input device to select or "snip" a portion 125p ("p" referring to "portion") of the currently displayed image 125. Snipping or selection action executed by interactive UI 124 serves as a trigger to capture pertinent data and generate a digital image report 360 for that currently displayed image 125 or selected portion 125p thereof. Digital image report 360 can then be transmitted as an electronic message to data store 220/PACS archive, other data store 330 or computing device 340.

Snipping application 350 may also be launched in response to other pre-determined user input based on voice recognition of a pre-determined verbal instruction spoken by user into input or peripheral device 127 in the form of a microphone of image review workstation 120A or by detection of a pre-determined gesture or motion detected by input or peripheral device 127 in the form of a camera of image review workstation 120A. Thus, embodiments not only provide for a "hands free" image snip and initiation of an image report, but post-snip actions such as verbal and video annotations may also be integrated into digital image report 360.

User may also specify verbal dimensions for a snipped area or snipping application 350 may select a pre-determined snipping radius from a certain point such as a location of a mouse cursor over the currently displayed image. Accordingly, the shape and dimensions of selected portion 125p of currently displayed image 125 may be drawn or specified by user or determined by image review workstation 120A automatically or based on user-provided dimensions. For ease of explanation, reference is made to selected portion 125p of currently displayed image 125. Having described how system embodiments may be configured and system component operability, embodiments are described in further detail with reference to FIGS. 4-10.

Figure 4:
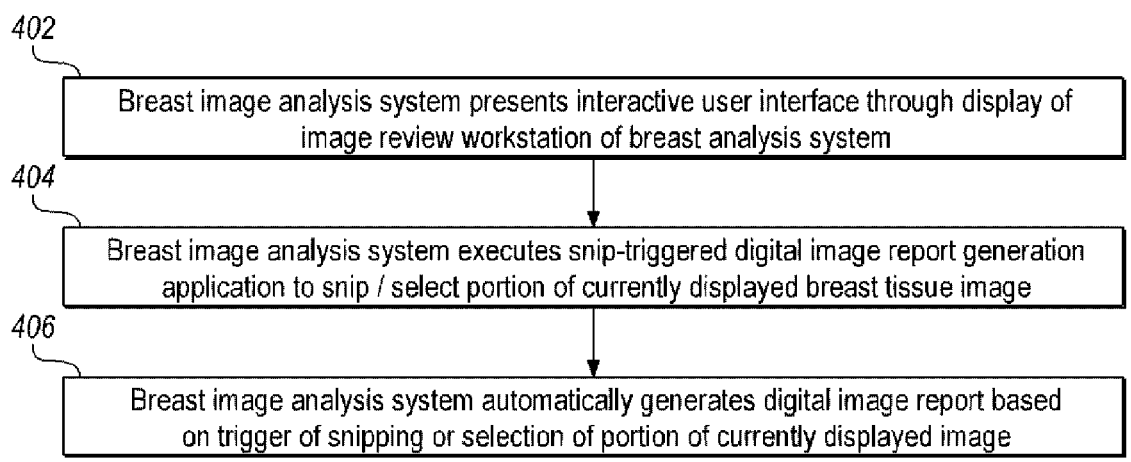
FIG. 4 is a flow diagram of one embodiment involving automated snip-triggered digital image report generation in a medical imaging environment.

Referring to FIG. 4, in a computer-implemented method 400 according to one embodiment, at 402, image review workstation 120A presents interactive UI 124 with currently displayed image 125 of breast tissue for a patient through display 122 of image review workstation 120A. At 404, image review workstation 120A receives user input to execute snipping application 350. At 406, image review workstation 120A, in response to the trigger of execution of snipping application 350, automatically generates digital image report 360 for snipped or selected portion 125p of currently displayed image 125.

Figure 5:
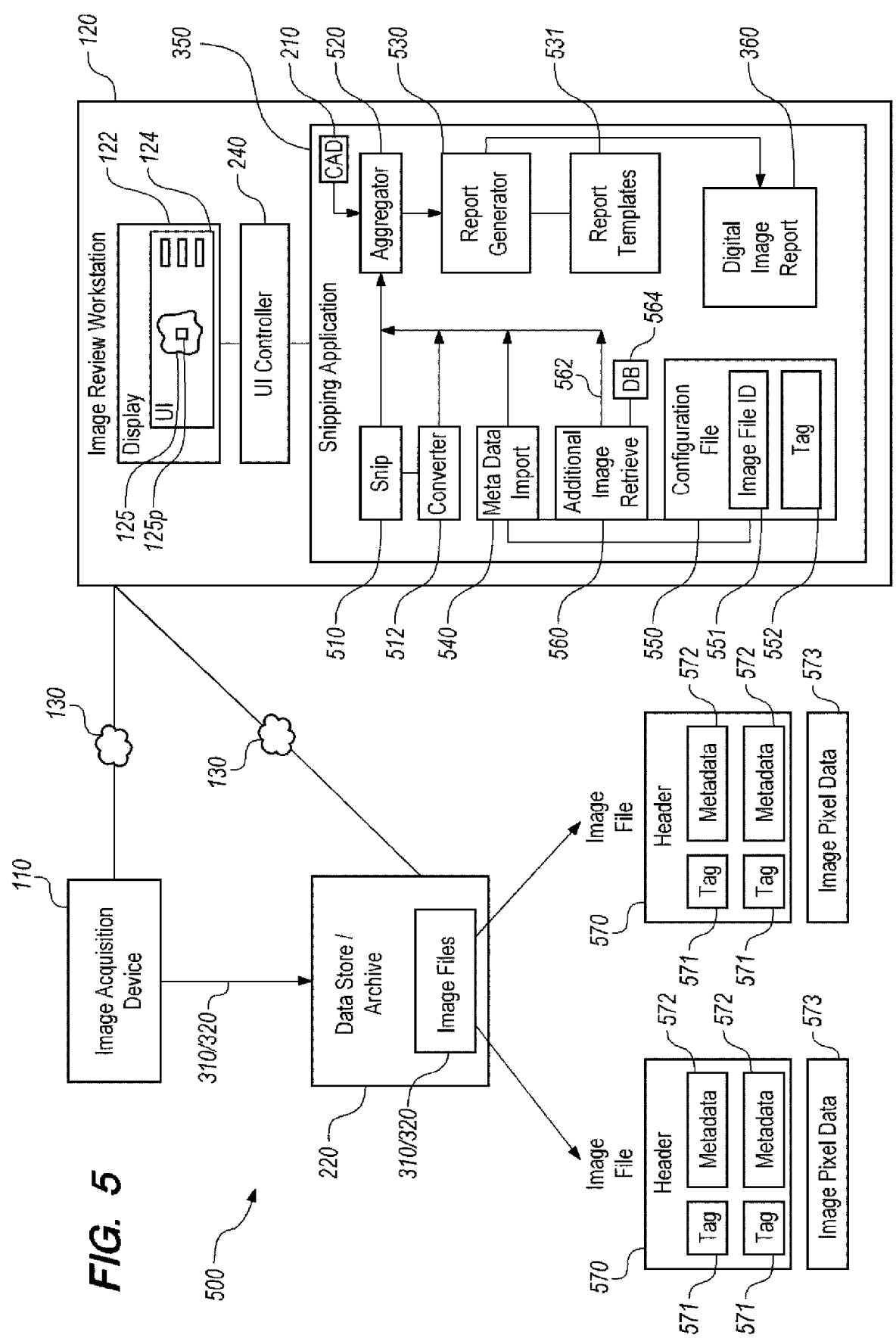
FIG. 5 is a system block diagram of a breast image analysis system constructed according to one embodiment and illustrating in further detail one manner in which a snipping application executed by an image review workstation ay be configured.

Referring to FIG. 5, breast image analysis system 500 or medical imaging environment configured according to one embodiment includes one or more image acquisition devices 110 in communication with image review workstation 120A, display 122 through which interactive UI 124 is displayed and with which user interacts, input devices 127 such as a mouse, keyboard, keypad, touchscreen, microphone or camera as discussed above, and data store 220 such as PACS archive, which stores image files 320 generated by image acquisition device 110 according to the DICOM standard. While embodiments are described with reference to DICOM standard and DICOM image files 320, it will be understood that embodiments are not so limited and that embodiments may be implemented using various image file standards.

In the illustrated embodiment, image review workstation 120A includes UI controller 240 for processing and displaying interactive UI 124 and user interactions with interactive UI 124 and snipping application 350 is in communication with UI controller 240 or a component of UI controller 240. In one embodiment, snipping application 350 is structured to include a snip function 510, an aggregator 520 and a report generator 530, which outputs digital image report 360. In other embodiments, snipping application 350 includes additional elements for other digital image report 360 capabilities and configurations including metadata import 540 and configuration file 550. In other embodiments, snipping application 350 also includes additional image identifier 560. Snipping application 350 may also include system generated data import to integrate system generated data 210 such as data generated by CAD processor or post-MRI processor for executing breast DCE colorization and providing kinetic findings. For these embodiments, system generated data sources such as CAD processor 210 also provide system generated data to aggregator 520. Other embodiments of snipping application 350 may import data from various combinations of sources noted above. Thus, the system configuration shown in FIG. 5 is provided as one example of how embodiments may be implemented. Individual components of snipping application 350, their operability and interoperability are described in further detail below.

Snip function 510 provides for snipping or selection of portion 125p of currently displayed image 125. Snip function 510 may output selected portion 125p in the image format of image file 320 standard (such as DICOM), or output generated by snip function 510 in the form of snipped or selected portion 125p of currently displayed image 125. Snip function 510 output may be provided as an input to a converter 512 to generate selected portion 125 in a different image format, e.g., to convert selected portion 125p from a DICOM format to a .jpeg format or other image format if digital image report 360 is to be generated with images of a certain format. While embodiments are described with reference to report 360 in an "image" format, embodiments may involve a generated report 360 that includes portions of multiple types or formats (image and non-image), and report 360 may also be a non-image format such as text, audio, video, JavaScript Object Notation (JSON), DICOM or Health Level 7 (HL7) format. Thus, "converter" 512 is not limited to an image format converter.

Snip function 510 is also in communication with aggregator 520, which is configured to collect images and data that are to be captured and incorporated into digital image report 360 to be generated. In the illustrated embodiment, aggregator 520 receives output or selected portion 125p generated by snip function 510.

Snipping application 350 may also include metadata import 540 that includes or reads configuration file 550 including pointers to or identifiers of certain portions of image files 320 in data store 220. In the illustrated embodiment, configuration file 550 includes a first identifier 551 utilized to locate image file 320 in data store 220 containing or corresponding to currently displayed image 125, and a second identifier 552 or additional identifiers of elements within image file 320 in the form of tags 571 utilized to identify and read certain metadata 572 of image file 320. Image file 320 may include a large number of tags 571 and associated metadata 572 related to, for example, patient demographic data, study and series data, and image acquisition data. Configuration file 550 is used to specify only a subset of image file tags 571 contained in image file 320. Tags 571 of configuration file 550 may be pre-set by the manufacturer of image review workstation or selected by the user of image review workstation 120A. Metadata import 540 is configured to communicate with data store 220, locate and access image file 320 stored in data store 220 and related to currently displayed image 125, and provide any metadata 572 identified using tags 571 retrieved from image file 320 to aggregator 520.

Aggregator 520 serves as a data collection element, or a type of temporary "clipboard," which provides collected data including selected portion 125p of currently displayed image, converted 512 versions thereof and any metadata 572 read from image file 320 to report generator 530. Aggregator 520 may also collect system generated data such as data generated by CAD processor 210 or post MRI processor.

Report generator 530 is configured to access an image report template 531 and populate image report template 531. According to one embodiment, template includes a section to be populated with selected portion 125p and other data collected by aggregator 520 and received by report generator 530 from aggregator 520. For this purpose, template 531 may have pre-defined fields or sections to be populated with images, pre-defined fields or sections to be populated with other data such as image file metadata 172 and system generated data.

In certain embodiments, snipping application 350, by additional image identifier 550, may also locate other images 552 related to or associated with currently displayed image 125 or selected portion 125p thereof, e.g., other images for the same patient and in a different series of images acquired on different dates during the course of imaging analysis and treatments. These other related images 552 may also be provided to aggregator 520 so that the digital image report 360 that is generated may include one or more or all of the snipped or selected portion 125p of currently displayed image 125, currently displayed image 125 itself, and one or more additional related images 552. Resulting image report 360 may also include retrieved metadata 572 for currently displayed image 125 and/or for other related images 552 and related system generated data (e.g., CAD and post MRI data) related to same. Further details of one embodiment of how a breast analysis system including an image acquisition device 110 and image review workstation 120A executing snipping application 350 operate are described with reference to FIGS. 6-10.

Figure 6:
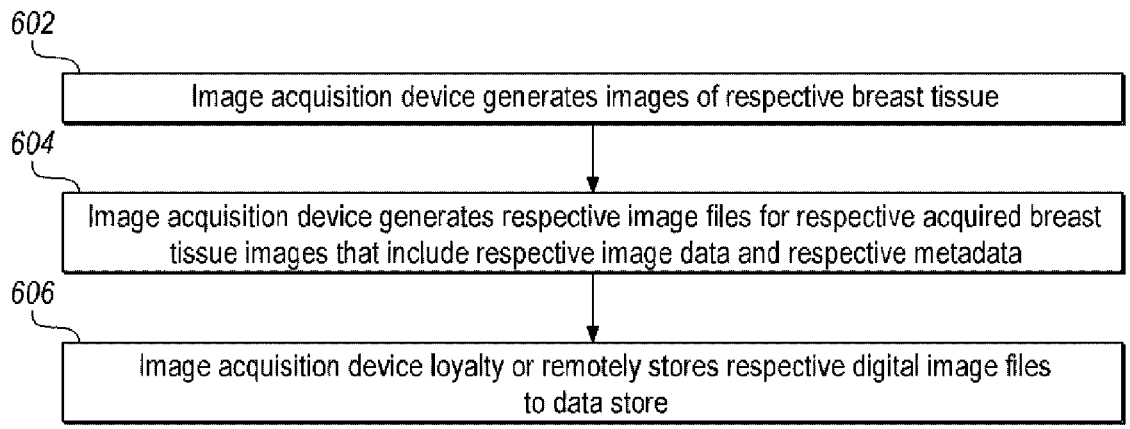
FIG. 6 is a flow diagram illustrating generation and storage of breast tissue image files by an image acquisition device.

Referring to FIG. 6, at 602, patient breast tissue is positioned or compressed by components of image acquisition device 110, such as a tomosynthesis imaging device, which generates digital images 310 of patient's breast tissue. At 604, image acquisition device 110 also generates respective digital image files 320 (e.g., DICOM files) for respective acquired breast tissue images/image data 310 or sets or series of images 310. This process may be repeated for different patients and for different series or dates for a given patient. At 606, image acquisition device 110 stores respective digital image files 320 containing images 310 or image 310 data to data store 220 such as PACS archive that is also accessible by image acquisition device 220.

Figure 7A:
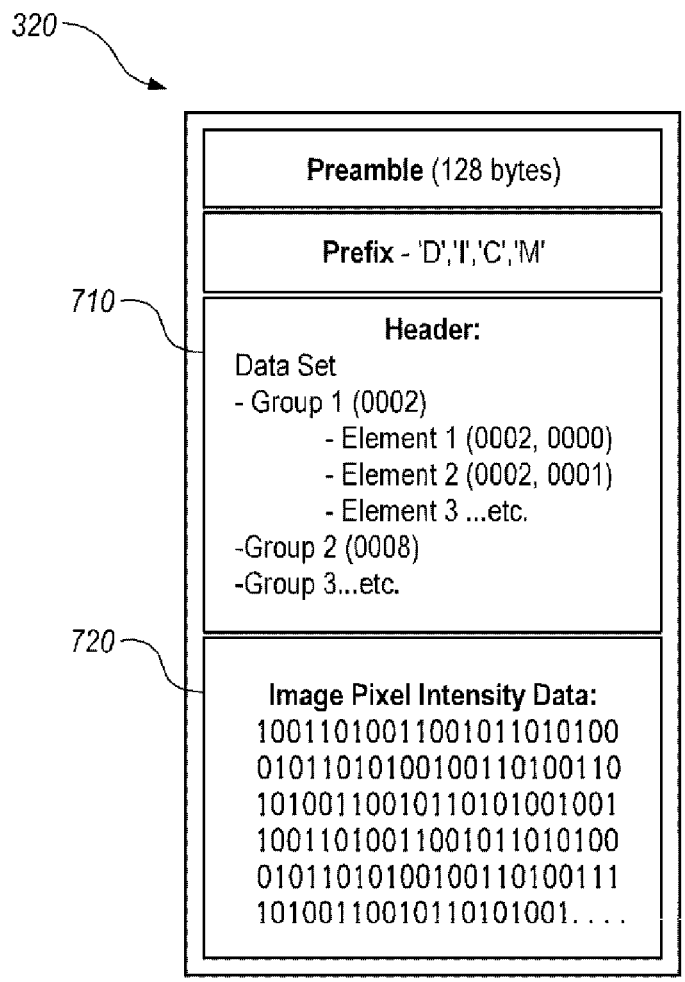
FIG. 7A depicts an image file structured according to a Digital Imaging and Communication in Medicine (DICOM) standard, and FIG. 7B illustrate examples of tags in a header of an image file structured according to the DICOM standard.

According to one embodiment, image files 320 are structured according to DICOM standard. FIG. 7A generally depicts how DICOM image file 320 generated by image acquisition device 310 is structured by grouping information into pre-defined data sets. As shown in FIG. 7A, image file 320 in the form of DICOM file includes a header 710 and image data 720. With further reference to FIG. 7B, header 710 contains various types of information about a breast imaging procedure including demographic or patient information, imaging parameters, and image acquisition device data. Header 710 is followed by intensity data 720 for the pixels of the image (binary 1s and 0s) and this data can be used to reconstruct an image or frames thereof.

Metadata 572 of DICOM image file 320 is referenced by respective tags 571, which serve as alpha-numeric pointers or references to corresponding metadata 572. For example, a DICOM header 710 may include identification or demographic information such as Patient ID referenced by tag (0010,0020), Patient Name referenced by tag (0010,0010). Header 710 may also include patient demographic information such as Patient's Age referenced by tag (0010,0101), Patient's sex referenced by tag (0010,0040). Header 710 may also include information about image acquisition device 110, image acquisition device 110 configuration, image attributes, and the imaging study being conduct. For example, header 710 may include information about acquisition date referenced by tag (0008,0022), type or format of data format utilized, e.g., video image format acquired by tag (0008, 1022) or digital image format acquired by tag (0008, 0123), and attributes or operating parameters of different types of image acquisition devices 110, e.g., whether MRI, CT, X-ray, or tomosynthesis. The DICOM standard uses hundreds of tags 571 referencing respective metadata 572 about the patient, images, image acquisition device, operating parameters, demographics, etc. While the types of DICOM tags 571 are comprehensive, the user of the image review workstation 120A is typically interested in only a subset, often a small subset, of available header 710 data. Image file 310 in form of a DICOM file also include a data set for image pixel intensity data 573, which can be used to reconstruct an image.

Figure 8:
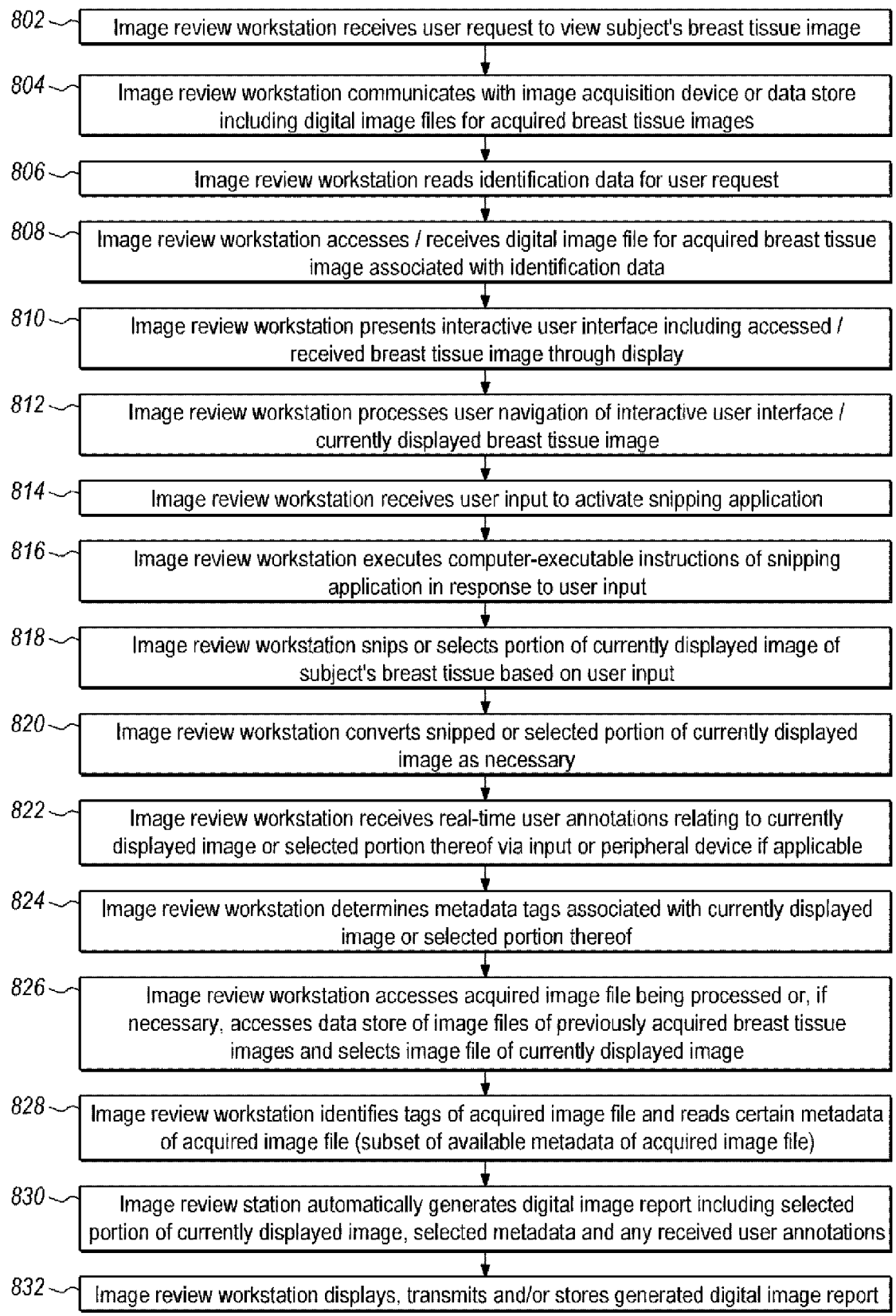
FIG. 8 is a flow diagram of one embodiment of a method for implementing snip-triggered digital image report generation within a medical imaging environment.

Referring to FIG. 8, following image acquisition device 110 acquiring images 310 and generating image files 320, image review workstation 120A receives a user request through interactive UI 124 to view subject's breast tissue image 310 at 802, and at 804, image review workstation 120A communicates with data store 220. At 806, image review workstation 120A reads a first or image file identifier of user request to locate the image file 310 in data store 220, and at 808, image review workstation 120A accesses or receives image file 320 or associated image data 720 to reconstruct requested image.

Figure 9A:
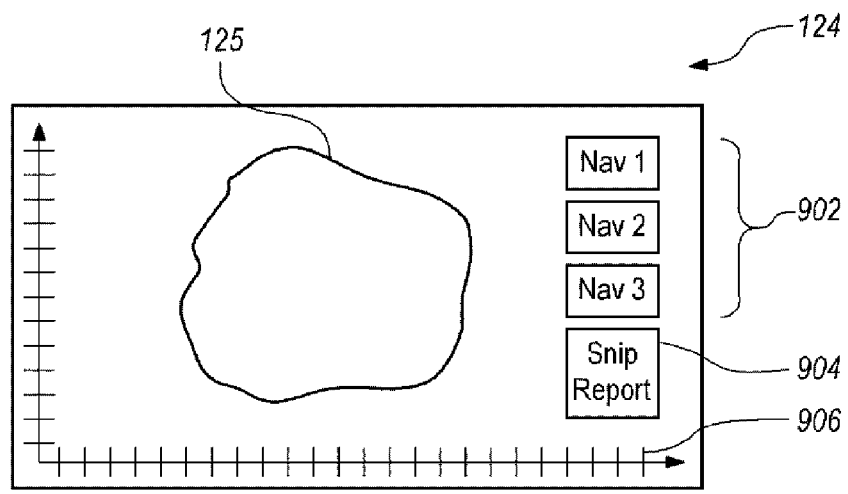
FIG. 9A depicts an interactive user interface presented through a display of an image review workstation.

At 810, and with further reference to FIG. 9A, image review workstation 120A, by UI controller 240, presents interactive UI 124 including the accessed or received breast tissue image, as generally depicted in FIG. 9A. In the illustrated example, interactive UI 124 includes currently displayed image 125 of breast tissue, navigation or workflow tools 902 (e.g., zoom in, zoom out, next image, prior image, next series, prior series, optical adjustments such as brightness, contrast, etc.) Interactive UI 124 may also include imaging, acquisition and lesion attribute data or UI elements to display such data, examples of which include capture markings and annotations, lesion measurements (size of lesion, including orthogonal measurements), lesion location (e.g., determined with reference to a ruler or other location/distance measurement, including for left and right breast, quadrant, o'clock region), and relative lesion distance information of lesion such as distance of a lesion from a chest wall or nipple of breast. User interacts with interactive UI 124, and at 812, image review workstation 120A, by UI controller 240, processes user navigation of interactive UI 124 and currently displayed image 125. As part of the review workflow, user may review various patient images, different image views, and images acquired using different imaging modalities.

In the illustrated embodiment, interactive UI 124 also includes an icon 904 for snipping application 350, which may be activated by user clicking on icon 904 with a mouse or by other input device 127, e.g., with a pre-determined key of a keyboard, a pre-determined verbal instruction spoken by user into microphone of image review workstation 120A, or by a pre-determined gesture detected by camera of image review workstation. For example, the user may select "Alt-S," ("s" for "snip"), click a certain button on a mouse, speak a pre-determined phrase such as "activate snip" into microphone or make a pre-determined gesture such as waving their hand in front of the camera or other pre-determined gesture to request execution of snipping application 350. For ease of explanation, reference is made generally to a snipping application 350 and activation of same based on a pre-determined user input.

Continuing with reference to FIG. 8, at 814, user has submitted input to request to activate snipping application 350, which is received by UI controller 240. At 816, and with further reference to FIG. 9B, processor of image review workstation 120A executes computer-executable instructions of snipping application 350 stored in non-tangible computer readable medium or read into memory in response to user input, and at 818, UI controller 240, by snip function 510 as shown in FIG. 9B, selects or crops portion of currently displayed image 125 of subject's breast tissue based on user input.

Figure 9B:
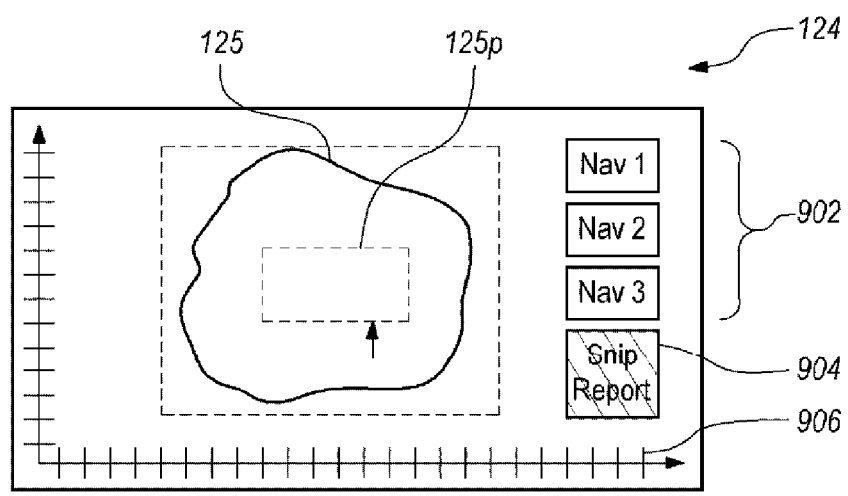
FIG. 9B depicts the interactive user interface and a portion of a currently displayed image being selected by activation of a snipping application according to embodiments.

According to one embodiment, as generally depicted in FIG. 9B, selection or snipping is executed based on user manipulation of a mouse, touchscreen, keyboard, keypad or other input device 127 that allows a user to define a snip area of selected portion 125p of currently displayed image 125. Selected portion 125p may include only a selected segment of the displayed tissue, or in other words, be defined within a boundary of tissue of currently displayed image 125 as illustrated in FIG. 9B, or selected portion 125p may encompass the entire displayed tissue. In other embodiments, snip function 510 automatically captures the entire displayed screen of interactive UI 124 without requiring user to define snip area. In yet other embodiments, snip function 510 captures a pre-defined area defined by a pre-defined radius or predefined vertical and horizontal distance from a pre-determined point. For example, pre-determined point may be a center of currently displayed image 125 or a current location of mouse pointer such that snip function 510 determines, e.g., with reference to ruler 906 measurements, e.g., 1 inch in each direction from mouse cursor to snip a square shape or snip a circular shape with a 1 inch radius. For ease of explanation, not limitation, reference is made to embodiments in which user defines snip area by manipulating mouse device 127 to define a selected portion of the currently displayed image 125. Referring again to FIG. 5, selected portion of currently displayed image is provided by snip function 510 to aggregator 520, which collects data to be utilized for digital image report 360 generation.

Referring again to FIGS. 5 and 8, at 820, if necessary, image review workstation 120A converts 512 snipped or selected portion 125p of currently displayed image 125 as necessary. For this purpose, as depicted in FIG. 5, output of snip function 510 in the form of selected portion 125p of currently displayed image 125 may be converted from a first image format a second image format, e.g., from a DICOM format to a .TIFF format, a .JPEG format, a .PNG format, or a .GIF format. Converter 512 may also be or include a non-image converter to generate audio, video, JSON or DICOM file as necessary, e.g., for capture of .AVI file for multiple image frames or a video of the interactive UI 124 to record user interactions interactive UI 124 to allow radiologist to review a video, scroll through slices or images of a slab or to review patient movement for MRI motion correction. Reference is made generally to converter 512 and embodiments may thus utilize the original DICOM format of the currently displayed image 125 without conversion, or convert 512 selected portion 125p of currently displayed image 125 from first image format to a different, second image format more for digital image report 360. Selected portion 125p of currently displayed image 125, whether converted or not converted, is provided by snip function 510 to aggregator 520.

With continuing reference to FIGS. 5 and 8, at 822, image review workstation 120A may receive real-time user annotations relating to currently displayed image 125 or selected portion thereof 125p via one or more of interactive UI 124 and input or peripheral device 127 if applicable, and these user provided annotations are also provided to aggregator 520. For example, user may enter notes, comments or observations via keyboard or touchscreen, and these annotations are received via interactive UI 124 and provided to aggregator 520. As another example, user may speak notes, comments or observations into microphone of image review workstation 120A, and the resulting audio file or text file resulting from audio to text conversion are provided to aggregator 520. As yet another example, image review workstation 120A may receive user annotations based on user input via a computer mouse, e.g., highlighting a certain part of captured screen or image portion or to point out certain data such as image, acquisition or demographic attributes or data.

It will be understood that user annotations may or may not needed and that user annotations may concern various aspects of the currently displayed image 125, patient, acquisition parameters, etc. For example, the user may provide comments or notes regarding the currently displayed breast tissue such as the amount of Fibroglandular Tissue (FGT), the amount and symmetry of background Parenchymal Enhancement (BPE), an observed lesion type or lesion attributes such as focus, mass, non-mass enhancement, skin lesion, intramammary Lymph Node, an observed fat-containing lesion or attribute such as lymph nodes and whether what is observed is normal, non-enhancing findings such as a cyst or non-enhancing mass, associated features such as architectural distortion, and whether any implants are observed.

Continuing with reference to FIGS. 5 and 8, in certain embodiments that also read metadata 572 from the acquired image file 320 for inclusion in digital image report 360 to be generated, image review workstation 120A determines identifiers or tags 571 of acquired image file 320 at 824. For this purpose, in the illustrated embodiment, snipping application 350 includes metadata import 540 that includes or reads configuration file 550 that specifies DICOM tags 571 used to read metadata 572 be read and provided to aggregator 520. In one embodiment, DICOM tags 571 can be specified or selected by the user before the user begins an image review workflow. In another embodiment, DICOM tags 571 are specified or selected by the user in real time during an image review workflow via interactive UI 124. User may review a list of possible DICOM tags 571 or tag categories (as shown in FIG. 7B) that can be selected. A DICOM image file 320 includes hundreds tags 571 for corresponding metadata 572, and configuration file 550 specifies a subset of available tags 571 for metadata 572 that is most pertinent or of interest to the image review workstation user or person who will be receiving the digital image report 360. Digital image report template 531 may also be configured to accommodate a limited number of types of metadata 572. In this manner, digital image report 360 is not cluttered with extraneous metadata 572 that is not needed or of interest.

In embodiments involving DICOM image files 320, configuration file 550 may include a list of DICOM tags 571 structured as eight alphanumeric elements (xxxx,yyyy) for identifying metadata 572 to be read from an acquired image file 320 associated with currently displayed image 125. For example, a first metadata tag 571 or first group of metadata tags 571 may be used to identify acquired image file 320 in data store 220 that was generated for currently displayed image 125 if it is necessary to access or retrieve acquired image file 320 that is the source of currently displayed image 125, e.g., if image review workstation 120A does not have a local copy of acquired image file 320. For this purpose, metadata import 540 may read a unique file identifier of currently displayed image 125 and locate corresponding identification data in data store 220 to identify corresponding acquired image file 320, or identify matching metadata 572 using tags 571 that can be used for unique identification such as one or more of Patient Name (0010,0010), Patient ID (0010,0020), Patient Birthdate (0010,0030), Patient Address (0010,1040), Patient Telephone Numbers (0010,2154), specified in configuration file 550.

As another example of how one embodiment may be implemented, configuration file 550 may identify a subset of DICOM header tags 571 for patient/demographic data such as patient name, data of birth and sex, study and series level information such as study date; study/series description, institution name, image acquisition device manufacturer, model and imaging modality, laterality, body part examined; and image level information such as image acquisition parameter data such as kilovolt peak (kVp) data, exposure data (mAs), dose data (ASD, ESD, EI), compression force, body part thickness, x-ray detector data, and filter data. It will be understood that configuration file 550 may specify various tags 571 for different types of metadata 572, and that the exemplary subset provided above is illustrative of types of DICOM tags 571 and associated metadata 572 that may be included in digital image report 360 and so that digital image report 360 content can be customized by the user of image review workstation 120A.

It will be understood that an acquired image file 320 corresponding to currently displayed image 125 can be identified using various unique identifiers, identifier tags and combinations thereof to ensure that the correct acquired image file 320 for currently displayed image 125 is identified, e.g., if multiple acquired image files 320 for a patient have been generated for prior diagnosis or treatments. Further, it will be understood that image review workstation 120A may utilize acquired image file 320 that is copied and stored locally at image review workstation 120A or image review workstation 120A may access acquired image file 320 stored in data store 220.

With continuing reference to FIG. 8, and referring again to FIG. 7B, at 828, image review workstation 120A accesses acquired image file 320 associated with currently displayed image 125 and, identifies tags 571 of configuration file 550, and reads respective metadata 572 associated with respective tags 571. Metadata 572 read from acquired image file 320 is provided by metadata import 540 to aggregator 520. At 830, and referring again to FIG. 5, image review workstation 120A automatically generates digital image report 360 incorporating the data collected. For this purpose, aggregator 520 provides data collected or retrieved from snip function 510, metadata import 540, image converter 512, user annotations and/or system generated data from CAD processor or post-MRI processor 210 as examples.

Report generator 530 populates respective portions of image report template 531 with respective image(s), converted images, user annotations, meta data and/or system generated data as appropriate.

Thus, resulting digital image report 360 may include one or more or all of the data elements collected by aggregator 520. For example, according to one embodiment, digital image report 360 includes only the selected portion 125p of currently displayed image 125 (in original DICOM format or in another image format after image conversion 512). According to another embodiment, digital image report 360 includes selected portion 125p of currently displayed image 125 and metadata 572 read from corresponding image file 320. According to a further embodiment, digital image report 360 includes selected portion 125p of currently displayed image 125 and user annotations or notes (whether recorded as text entered via keyboard, touchscreen, mouse highlights or notations, an audio file generated by user speaking into microphone for annotations, text resulting from conversion of the audio file, or a video file of the user's interactions with the interactive UI 124). According to another embodiment, digital image report 360 includes selected portion 125p of currently displayed image 125, user annotations and metadata 571 of corresponding acquired image file 320. According to other embodiments, digital image report 360 includes system generated data such as CAD or kinetics findings generated by CAD or post MRI processor 210.

Thus, it will be understood that generated image report 360 may integrate various types eps of data received from aggregator 520, and that the resulting image report 360 may or may not include metadata 571 read from image file 320. It will also be understood that digital image report 360 and components thereof provide by aggregator 520 may be in various formats depending on the desired output format of digital image report 360 and content thereof. For example, digital image report 360 or components thereof may be in a standard format such as a .TIFF format, a JPEG format, a .PNG format, a .GIF format or a non-image format such as audio format or video format such as .AVI. Further, digital image report 360 or components thereof may be structured according to non-image formats such as DICOM format or series (e.g., derived series with Referenced Service-Object Pair (SOP) class, Instance Unique Identifiers (UID) and HL7. Digital image report 360 may also be configured as a text file for cases in which digital image report 360 includes information about an image but not an image itself, or portions of digital image report 360 may be in the form of a text file. In another embodiment, digital image report 360 may be in the form of a clipboard structure that serves as a temporary file or storage such that the data of digital image file can be copied to a Word or PowerPoint file. Digital image report 360 may also be configured as a delimited text file (e.g., based on National Mammography Database (NMD) file specifications, which may also be exported and submitted to NMD or other reporting system. Digital image report 360 may also be structured according to a user or manufacturer defined container format, which may be open to the public and that can be integrated with external reporting and dictation systems. Accordingly, it will be understood that digital image report 360 or particular sections or content thereof may be structured in different ways, and that digital image report 360 may be structured according to a single or multiple data formats.

With continuing reference to FIGS. 5 and 8, at 832, image review workstation 120A may execute one or more post image report generation actions such as presenting digital image report 360 through display 122 of image review workstation 120A, storing digital image report 360 in local data store 330, transmitting digital image report 360 to data store 220 or PACS archive, and for this purpose, digital image report 360 may be stored together with or linked to corresponding acquired image file(s) 320. Image review workstation 120A may also transmit digital image report 360 through communication network 130 to user computer 340 for subsequent review after the image review workflow with image review workstation 120A has been completed. The user computer 340 may be connected to the data store 220 through the communication network 130.

In some embodiments, the user computer 340 is another image review workstation similar to the workstation 120A, where the user may either retrieve the digital image report 360 via data store 220 or PACS archive or may directly receive the digital image report 360 through communication network 130. A user of the user computer 340 may include a radiologist. The radiologist may access the digital image report 360 and the other image review workstation may access the metadata 572 and the image file 320, including any tags or annotations. The radiologist may then validate the conclusion of the first user or radiologist reached in the first review. The radiologist may then access the images described and included in the digital image report 360 for validation and conclusion or use the information for further diagnosis or treatment.

In other embodiments, the user computer 340 may be a computer system accessed by a technologist for further diagnostic imaging. The user computer system may be similar to the acquisition workstation 120 shown in FIG. 1. The technologist may acquire additional images based on the information and images contained in the digital image report 360.

In additional embodiments, the user computer 340 may be part of a patient reporting system and may use the information contained in the digital image report 360 to generate reports provided to a patient imaged by systems 110a-e.

While certain embodiments have been described above with reference to snip-triggered generation of a digital image report 360 including a selected portion 125p of a currently displayed image 125, other embodiments involve incorporating multiple selected portions 125p of currently displayed image 125. Yet other embodiments involve incorporating additional images or additional image portions, or other views thereof, into the digital image report 360 such that the digital image report 360 includes at least two images or portions thereof. Such digital image reports 360 may also include one or more or all of metadata 372 from one or more or all of respective image files 320, user annotations, converted images and system generated data. Embodiments involving multiple or additional image captures allow for consolidation of multiple captures into a single digital image report 360 for even more comprehensive assessment that may involve, for example, patient level assessment, left/right breast assessment, fibroglandular tissue (FGT) and background parenchymal enhancement (BPE) assessment, and assessments of a combination of different procedures or results of different imaging modalities and results generated thereby.

For these purposes, currently displayed image 125 may include a reference to other images or other image views, e.g., as stored in the data store 220. Thus, while a portion 125p of currently displayed image 125 is selected or snipped, snipping application 350 executes to locate other related images or other views of the currently displayed image or portion thereof.

Referring again to FIG. 5, breast image analysis system or medical imaging environment constructed according to one embodiment includes components described above with reference to FIG. 5 and further provides for additional image retrieval 560. Additional images 562 to be retrieved can be identified by database 564 of acquired images, including the currently displayed image 125, and references to other images 562 to be retrieved. Further aspects of embodiments are described with reference to FIG. 10, and various system and operability details described above are not repeated.

Figure 10:
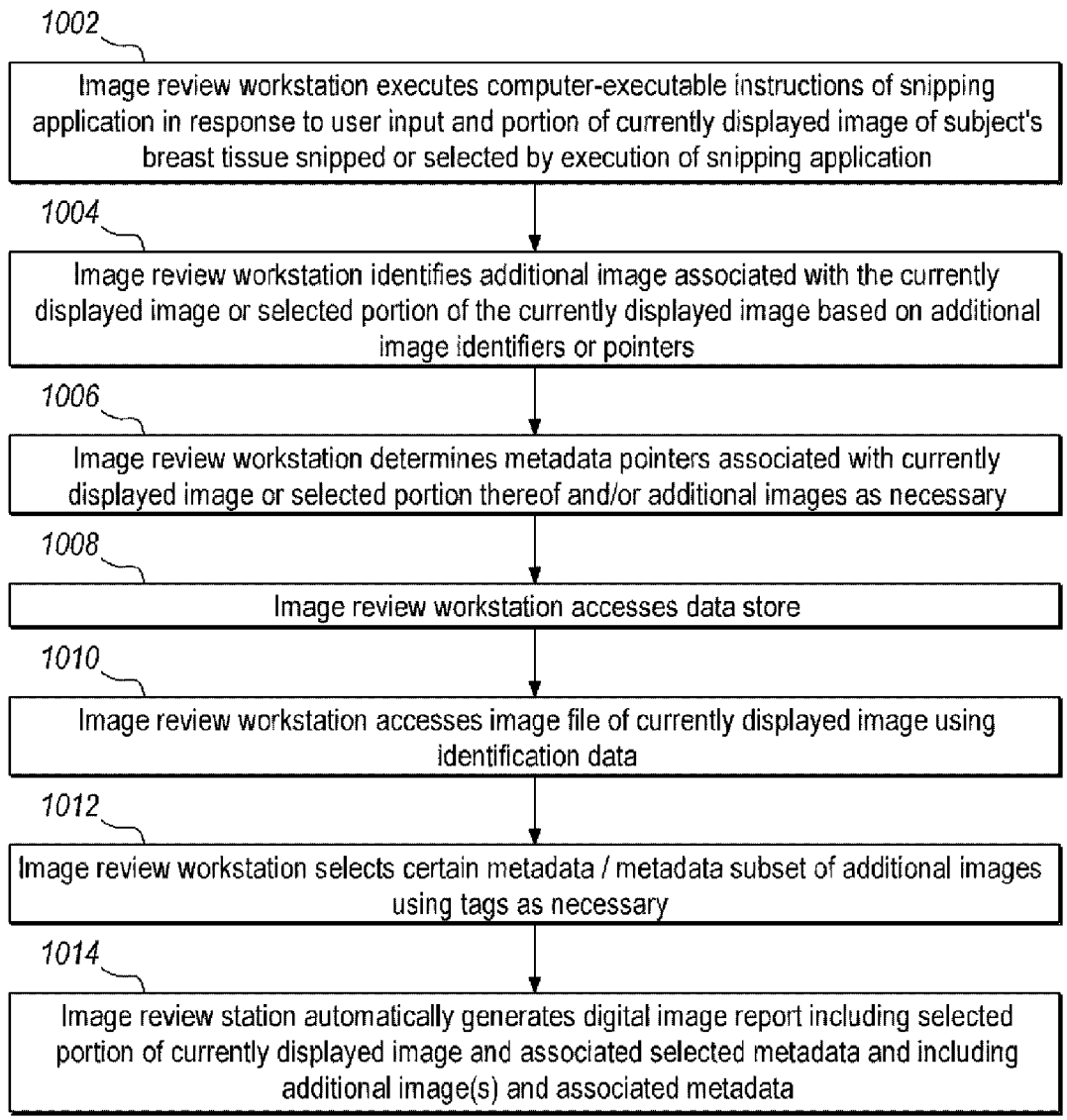
FIG. 10 is a flow diagram of one embodiment of a method for implementing snip-triggered digital image report generation within a medical imaging environment and how additional related images can be identified and incorporated into the digital image report.

Referring to FIG. 10, at 1002, image review workstation 120A executes computer-executable instructions of snipping application 350 in response to user input, and a portion 125p of currently displayed image 125 of subject's breast tissue snipped or selected. At 1004, snipping application 350 identifies one or more additional images 562 associated with the currently displayed image 125. The one or more additional images 562 may be additional images of the same view (e.g., image of same view for same patient at an earlier date to provide for image comparison), additional images 562 of different views of the currently displayed image or different views of the selected portion of the currently displayed image 125 to provide a different visual perspective of the selected portion of the currently displayed image of interest, or a combination thereof. For this purpose, additional image retrieval 560 may maintain or access a database 564 cross referencing images and related views of the currently displayed image 125, which may be in the same data store or archive or different data stores. At 1006, snipping application 350, using data store pointers or identifiers, address data and/or related image identifiers in database 564, accesses the referenced data store to access or retrieve additional images 562 at 1008, and at 1010, image review workstation 120A reads or makes a copy of the additional image file related to the currently displayed image 125. At 1012, image review station 120A may also access configuration file 550 to determine DICOM tags 571 to retrieve metadata 572 about the additional images 562 or image views, and at 1014, performs image conversion 512 as necessary. Additional images 562 and any metadata 572 and converted 512 images are provided to aggregator 520 such that aggregator 520 includes selected portion 125p of currently displayed image 125 and at least one additional image 562 related to currently displayed image 125, an image 562 of a different view of currently displayed image 125 and an image 562 of a different view of selected portion 125p of currently displayed image 125. Image 562 of different view of selected portion 125p may be identified, selected and aligned with reference to ruler measurements 906, dimensions and distance data of selected portion 125p of currently displayed image 125. Such measurements, dimensions and distance data can be used in another image or other view 562 to identify selected portion 125p in the other image or view 562. Aggregator 520 may also include one or more or all of converted images, user annotations and metadata 572 concerning the selected portion 125p of currently displayed image 125 and/or one or more or all of the additional images 562. At 1014, image review station 120A automatically generates digital image report 360 including selected portion 125p of currently displayed image 125 and at least one additional image 562, and in certain embodiments, associated selected metadata 572.

For example, currently displayed image 125 is presented through interactive UI 124 in a first view such as an axial view of selected portion 125p. Image review workstation 120A identifies selected portion 125p of currently displayed image 125 using one or more of interface ruler 906, measurements or relative dimensions in a second view (or third or other view). For example, the first view may be an axial view of the selected portion of the currently displayed image, and the second view may be a sagittal view or a coronal view of the selected portion of the currently displayed image. In cases in which a third view is utilized, the second view is one of the sagittal view and the coronal view, and the third view is the other of the sagittal and coronal view.

As another example of how embodiments may be implemented, the second view is a computer-generated rendering of selected portion 125p of currently displayed image 125 such as a maximum intensity projection rendering, multiplanar reconstruction rendering, a subtraction rendering, a CAD rendering or an MRI processed output such as a rendering of breast DCE decolorization. As a further example, a first view may be based on an acquired optical image of the subject's breast tissue, and a second view is a computer-generated rendering of the subject's breast tissue.

Embodiments involve additional images 562 acquired by the same acquisition device 110 and modality, which may also be part of the same image file 320. In another embodiment, additional image 562 is acquired by a different acquisition device 110 using a different imaging modality, and additional image 562 is part of a different image file 320. For example, currently displayed image 125 may have been generated by a first image acquisition device 110 in the form of MRI device, whereas an additional image 562 was generated by a second image acquisition device 110 such as one of a tomosynthesis imaging device, an x-ray imaging device, or an ultrasound imaging device.

Thus, it will be understood that embodiments may identify additional images 562 of the same type, of different types, acquired using the same device/modality, different devices/modalities, and that the additional images 562 may be images of the currently displayed image 125 or selected portion 125p thereof, as well as different views thereof, and that these additional images 562 can be provided to aggregator 520 for incorporation into digital image report 360 to be generated.

Embodiments thus provide for efficient and automated digital image report generation that is in-line with a current review workflow while also providing for more comprehensive image reports to reduce errors and provide additional image data as a result of being able to incorporate one or more or all of images, metadata, system generated data and user annotations automatically into a single digital image report while eliminating or reducing the need for manual entry of such data which can be very cumbersome and interrupts the user's workflow. Embodiments also provide for more effective tracking of tumor response criteria, e.g., as set forth in Response Evaluation Criteria in Solid Tumors (RECIST), which is a widely accepted standardized measure of tumor response and establishes definitions for minimum size of measurable lesions, instructions about how many lesions to follow, and the use of unidimensional measures for tumor evaluation.

Embodiments also enhance engineer image reviews when attempting to identify and resolve software issues related to how images based on the same image acquisition data appear differently when using different software programs and thus enhancing troubleshooting the sources of image inconsistencies. Embodiments also enhance radiologist review and workflows by providing for the ability to not only request generation of a digital image report during a workflow, but also being able to specify the digital image content report for a more comprehensive summary without being interrupted or having to utilize a different computing system to prepare a report or record notes and observations.

While certain embodiments have been described individually, other embodiments may involve a combination of those individually described embodiments.

For example, while certain embodiments have been described with reference to generation of a digital image report based on an image snip, it will be understood that embodiments may involve generation of a complete digital image report or partially populating or generating a digital image report. As another example, while certain embodiments have been described with reference to generation of a digital image report in certain exemplary formats, it will be understood that other image formats may be utilized, and that a report may also be in, or contain portions in, a non-image format such as text, video, JSON or DICOM, HL7 and proprietary formats. Moreover, while certain embodiments are described with reference to a generated image report including a selected portion of an image, it will be understood that a generated image report may include one or more or all of the currently displayed image, the selected portion of the currently displayed image, one or more other related images or selected portions thereof that are not displayed to the user. Additionally, while certain embodiments are described with reference to snip triggered generation of a digital report and associated images and image metadata, it will be understood that embodiments may involve generation of a complete or partial digital report in a certain format including one or more or all of a currently displayed image or selected portion thereof (or images and portions thereof), another image that is not currently displayed or certain portion thereof, and associated data including one or more or all of image metadata (patient, study, series, image), user input or annotations (such as spoken annotations and measurements), and system generated input (e.g. kinetics, CAD data), and that the report format may be an image or non-image format.

While multiple embodiments and variations of aspects of the invention have been disclosed herein, such disclosure is provided for purposes of illustration only. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process as well as performed sequentially. Thus, the methods shown in various flow diagrams and described with reference to particular snipping application configurations and execution are not intended to be limited to a particular sequential order, particularly in instances in which certain steps may or may not be performed. Accordingly, embodiments are intended to exemplify alternatives, modifications, and equivalents that may fall within the scope of the claims.

The invention claimed is:

1. A computer-implemented method, comprising:
an image review workstation generating an electronic digital image report automatically triggered in response to snipping a portion of a currently displayed image of an interactive user interface presented by the image review workstation, the automatically triggered electronic digital image report being based on at least a portion of metadata associated with the currently displayed image; and
the image review workstation transmitting the electronic digital image report from the image review workstation to a computing device through a communication network, wherein the digital image report is presented to a user of the computing device through a display of the computing device;

wherein snipping a portion of the currently displayed image comprises selecting the portion of the currently displayed image on the interactive user interface, and wherein the electronic digital report comprises at least the currently displayed image and the metadata.

2. The computer-implemented method of claim 1, wherein the metadata included in the digital image report is selected by the user of the image review workstation before activation of the snipping application.

3. The computer-implemented method of claim 1, wherein the metadata included in the digital image report is selected by the user of the image review workstation after activation of the snipping application and during use of the image review workstation.

4. The computer-implemented method of claim 3, further comprising the image review workstation, in response to selection of the portion of the currently displayed image:
presenting to the user types of metadata of the identified acquired image file that may be included in the digital image report; and
receiving user input selecting certain metadata of the identified acquired image file,
the generated digital image report including the selected certain metadata.

5. The computer-implemented method of claim 1, the generated digital image report comprising patient demographic data, study and series data, and image acquisition data of the acquired image file associated with the selected portion of the currently displayed image.

6. The computer-implemented method of claim 1, the currently displayed image being presented through the interactive user interface in a first view, further comprising the image review workstation identifying the selected portion of the currently displayed image in a second view different from the first view, the digital image report comprising the selected portion of the currently displayed image as presented in the first view and the selected portion of the currently displayed image as presented in the second view.

7. The computer-implemented method of claim 1, further comprising the image review workstation:
identifying an additional image associated with the currently displayed image; and
identifying a portion of the additional image corresponding to the selected portion of the currently displayed image,
the digital image report comprising the identified portion of the additional image.

8. The computer-implemented method of claim 1, further comprising the image review workstation receiving, by a user input device, real-time user annotations concerning the selected portion of the currently displayed image, the digital image report comprising the user annotations.

9. The computer-implemented method of claim 1, the interactive user interface further comprising capture indicators of at least one of measurement data, location data and distance data associated with a lesion depicted in the selected portion of the current displayed image.

10. The computer-implemented method of claim 1, wherein a digital image report template is generated by the image review workstation automatically in response to activation of the snipping application, and the digital image report template is automatically populated by the image review workstation to generate the digital image report in response to user selection of the portion of the currently displayed image.

11. The computer-implemented method of claim 1, wherein the digital image report is automatically generated by the image review workstation without manual entry of the metadata by the user.

12. A breast image analysis system implementing the method of claim 1, wherein the image review workstation is configured to receive images acquired by a breast image acquisition system.

13. The computer-implemented method of claim 1, wherein the digital image report is in a digital imaging and communications in medicine (DICOM) format.

14. The computer-implemented method of claim 1, wherein the metadata comprises at least one of patient demographic data, study data, series data, and image acquisition data.

15. A computer-implemented method, comprising:
an image review workstation receiving an electronic digital image report, through a communication network, wherein the digital image report is based on at least a portion of metadata associated with a currently displayed image and comprises a portion of the currently displayed image snipped by a user of an interactive user interface presented by another image review workstation using a snipping application, and wherein a generation of the electronic digital image report is automatically triggered in response to snipping of the displayed image by the user; and
displaying the digital image report to a user of the image review workstation through a display;
wherein the electronic digital report comprises at least the currently displayed image and the metadata.

16. The computer-implemented method of claim 15, wherein the metadata included in the digital image report is selected by the user of the other image review workstation before activation of the snipping application.

17. The computer-implemented method of claim 15, wherein the metadata included in the digital image report is selected by the user of the other image review workstation after activation of the snipping application and during use of the other image review workstation.

18. The computer-implemented method of claim 15, the generated digital image report comprising patient demographic data, study and series data, and image acquisition data of the acquired image file associated with the selected portion of the currently displayed image.

19. The computer-implemented method of claim 15, the displayed image being presented through the interactive user interface in a first view, further comprising the image review workstation identifying the selected portion of the currently displayed image in a second view different from the first view, the digital image report comprising the selected portion of the currently displayed image as presented in the first view and the selected portion of the currently displayed image as presented in the second view.

20. The computer-implemented method of claim 15, further comprising the image review workstation:
identifying an additional image associated with the currently displayed image; and
identifying a portion of the additional image corresponding to the selected portion of the currently displayed image,
the digital image report comprising the identified portion of the additional image.

21. The computer-implemented method of claim 15, the digital image report further including real-time user annotations concerning the selected portion of the displayed image, the digital image report comprising the user annotations.

22. The computer-implemented method of claim 15, wherein the digital image report is automatically generated by the other image review workstation without manual entry of the metadata by the user.

23. A breast image analysis system implementing the method of claim 15, wherein the image review workstation is configured to receive images acquired by a breast image acquisition system.

24. The computer-implemented method of claim 15, wherein the digital image report is in a digital imaging and communications in medicine (DICOM) format.

25. The computer-implemented method of claim 15, wherein the metadata comprises at least one of patient demographic data, study data, series data, and image acquisition data.

* * * * *